(12) United States Patent
Fleischer et al.

(10) Patent No.: US 10,952,679 B2
(45) Date of Patent: *Mar. 23, 2021

(54) METHOD AND DEVICE FOR IMPROVING PREDICTION AND DETECTION OF ADVERSE EVENTS IN ELDERLY OR DISABLED PEOPLE

(71) Applicant: ReQbo Aps, Aarhus N. (DK)

(72) Inventors: Jesper Fleischer, Aarhus (DK); Anders Geert Jensen, Aarhus (DK)

(73) Assignee: ReQbo Aps, Aarhus N. (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/816,343

(22) Filed: Mar. 12, 2020

(65) Prior Publication Data

US 2020/0253557 A1 Aug. 13, 2020

Related U.S. Application Data

(63) Continuation of application No. 16/362,755, filed on Mar. 25, 2019, now Pat. No. 10,624,585, which is a (Continued)

(30) Foreign Application Priority Data

Oct. 5, 2012 (DK) .......................... PA 2012 70605

(51) Int. Cl.
*A61B 5/00* (2006.01)
*A61B 5/103* (2006.01)
*G08B 21/18* (2006.01)

(52) U.S. Cl.
CPC .......... *A61B 5/6892* (2013.01); *A61B 5/1036* (2013.01); *A61B 5/1038* (2013.01);
(Continued)

(58) Field of Classification Search
CPC ..... A61B 5/6892; A61B 5/746; A61B 5/7405; A61B 5/1038; A61B 5/6807; A61B 5/447;
(Continued)

(56) References Cited

U.S. PATENT DOCUMENTS 5,471,405 A 11/1995 Marsh
5,500,635 A 3/1996 Mott
(Continued)

*Primary Examiner* — Nader Bolourchi
(74) *Attorney, Agent, or Firm* — Dave Law Group LLC; Raj S. Dave

(57) ABSTRACT

Embodiments relates to a method, apparatus and system comprising a resting device for resting a patient, the resting device comprising a substrate having a contact surface for contacting the patient, one or more sacs comprising a material and associated with the contact surface of the substrate, one or more sensors that are incorporated in the one or more sacs, and a patient recognition algorithm to detect changes in a user profile; wherein the system is configured to at least (a) combine information and construct the user profile, wherein the information comprises a first data from a pressure ulcer risk scale and a second data obtained via the resting device over time, and (b) automatically perform an assessment of a risk of pressure ulcer in the patient.

21 Claims, 18 Drawing Sheets

Related U.S. Application Data continuation of application No. 15/595,599, filed on May 15, 2017, now Pat. No. 10,238,342, which is a continuation-in-part of application No. 15/583,989, filed on May 1, 2017, now Pat. No. 10,123,734, which is a continuation of application No. 14/433,597, filed as application No. PCT/IB2013/002919 on Oct. 7, 2013, now Pat. No. 9,636,045.

(60) Provisional application No. 62/336,084, filed on May 13, 2016.

(52) U.S. Cl.
CPC .............. *A61B 5/447* (2013.01); *A61B 5/6807* (2013.01); *A61B 5/742* (2013.01); *A61B 5/7405* (2013.01); *A61B 5/746* (2013.01); *A61B 5/7455* (2013.01); *G08B 21/182* (2013.01); *A61B 2562/029* (2013.01); *A61B 2562/0247* (2013.01); *A61B 2562/0271* (2013.01)

(58) Field of Classification Search
CPC ..... A61B 5/7455; A61B 5/1036; A61B 5/742; A61B 2562/0271; A61B 2562/0247; A61B 2562/029; G08B 21/182
See application file for complete search history.

(56) References Cited

U.S. PATENT DOCUMENTS

| | | |
|---|---|---|
| 5,642,096 A | 6/1997 | Leyerer et al. |
| 6,430,843 B1 | 8/2002 | Potter et al. |
| 7,726,206 B2 | 6/2010 | Terrafranca, Jr. et al. |
| 8,185,181 B2 | 5/2012 | Feldman et al. |
| 8,384,551 B2 | 2/2013 | Ross et al. |
| 9,050,041 B2 | 6/2015 | Feldman et al. |
| 10,624,585 B2 | 4/2020 | Fleischer et al. |
| 2004/0074966 A1 | 4/2004 | Holzer |
| 2005/0261609 A1 | 11/2005 | Collings et al. |
| 2006/0248750 A1 | 11/2006 | Rosenberg |
| 2007/0173903 A1 | 7/2007 | Goren et al. |
| 2008/0169931 A1 | 7/2008 | Gentry et al. |
| 2009/0135001 A1 | 5/2009 | Yuk |
| 2009/0137933 A1 | 5/2009 | Lieberman et al. |
| 2009/0192364 A1 | 7/2009 | Voto et al. |
| 2010/0036269 A1 | 2/2010 | Ferren et al. |
| 2010/0283630 A1 | 11/2010 | Alonso |
| 2011/0054359 A1 | 3/2011 | Sazonov et al. |
| 2011/0068935 A1 | 3/2011 | Riley et al. |
| 2011/0214501 A1 | 9/2011 | Ross et al. |
| 2011/0263950 A1 | 10/2011 | Larson et al. |
| 2014/0039351 A1 | 2/2014 | Mix et al. |
| 2014/0182049 A1 | 7/2014 | Prust et al. |
| 2015/0250426 A1 | 9/2015 | Muehlsteff |
| 2016/0022218 A1 | 1/2016 | Hayes et al. |
| 2018/0125414 A1* | 5/2018 | Lafleche et al. ....... A61B 5/447 |

\* cited by examiner mMETHOD AND DEVICE FOR IMPROVING
PREDICTION AND DETECTION OF
ADVERSE EVENTS IN ELDERLY OR
DISABLED PEOPLE

RELATED APPLICATION

This application is a continuation of U.S. patent application Ser. No. 16/362,755, filed on Mar. 25, 2019 which is a continuation of U.S. patent application Ser. No. 15/595,599, filed on May 15, 2017 (now U.S. Pat. No. 10,238,342, issued on Mar. 26, 2019), which claims the benefit of priority of U.S. Provisional Application No. 62/336,084, filed May 13, 2016, and is a continuation-in-part of U.S. patent application Ser. No. 15/583,989, filed on May 1, 2017 (now U.S. Pat. No. 10,123,734, issued Nov. 13, 2018), which is a continuation of U.S. patent application Ser. No. 14/433,597, filed Apr. 3, 2015 (now U.S. Pat. No. 9,636,045, issued May 2, 2017), which is the U.S. national phase entry of International Patent Application No. PCT/IB2013/002919, filed on Oct. 7, 2013, which claims the benefit of foreign priority of Danish Patent Application No. PA 2012 70605, filed on Oct. 5, 2012, and all of the above applications are herein incorporated in their entirety by reference.

TECHNICAL FIELD

This disclosure relates generally to monitoring and prevention of health-related conditions of a person, and in particular, to a method and apparatus for monitoring and preventing pressure ulcers and for risk stratification, monitoring, detection and prediction of adverse events in bedridden people.

BACKGROUND ART

Elderly, bedridden patients, wheelchair bound patients, people with limited mobility or reduced sensation of touch, e.g. those suffering from diabetic neuropathy, have high risk of developing adverse events. Pressure ulcers, also called bed sores, are a major health issue. Bedridden patients, wheelchair bound patients, people with limited mobility or reduced sensation of touch, e.g. those suffering from diabetic peripheral neuropathy, have high risk of developing pressure ulcers. Pressure ulcers (PUs) can develop quickly and are painful for the patient. They are generally resistant to known medical therapy and, are often very difficult to heal. PUs can cause reduced anatomical or functional integrity in patients and can, occasionally lead to life threatening complications. Care for patients suffering from PUs is often time consuming, personnel intensive and expensive. Once developed, PUs increased hospital stay, imposing enormous burden on the healthcare system and diverting precious personnel resources that may be allocated for other patients. Pressure ulcers, also called bed sores, are a major health issue. Furthermore, day-to-day increased in body temperature or weight loss will increase the risk of PUs and may by a symptom of another advance event like dehydration.

Either static or long-term dynamic or punctual load, which allows pressure marks on an insensitive or passive area on the body, can lead to pressure ulcers if not taken care of in time. Such occurrences of pressure can occlude blood supply to parts of the body leading to tissue ischemia. If such pressure is not relieved over a long period of time tissue ischemia can lead to permanent cell damage causing pressure ulcers. The person with normal sensation and mobility would be immediately alerted while the person without sensation or reduced mobility—allows repeated high pressure and/or static load on the same small place on the body. This can create sores or precursors thereof.

For example, patients suffering from diabetic neuropathy have reduced sensation in their extremities and may not sense a wound or skin damage to their hands and/or feet. In such patients, a wound or skin damage on the foot can occur without detection, and the condition can lead to complications such as severe infection, slow healing wounds and risk of amputation. Therefore it becomes important for staff at the hospital or nursing home to constantly monitor vulnerable areas of the body and especially observe pressure related alteration of the skin that may be precursors of pressure ulcer.

So far, the most effective care for an at-risk patient is to relieve the pressure which, in hospitals, is commonly done by periodically repositioning bed-bound patients. Because every patient has levels of risk of occurrence of PUs depending on factors such as age, sex, disease conditions, blood pressure, nutrition, etc., some patients may need more frequent repositioning than others. Determining the schedule for repositioning is difficult may yet be unable to prevent occurrence of PUs.

Existing pressure relieving massage mattresses with inflatable chambers, where the different chambers are inflated and deflated in different intervals. The desired effect of these massage mattresses are relocation of the weight loads of the patient prolonging the time span the patient is able to be in the same position without developing a PU. These massage mattresses do not reposition the patient which is vital to avoid PU's and they increase the shear stress on the patient skin while inflating and deflating, which may also lead to develop PU's.

Devices for monitoring patients to prevent and/or detect PUs generally include an array of pressure sensors placed in close proximity to parts of a patient's body that are at a higher risk of forming PUs. The pressure sensors record pressure on the at-risk parts and provide the data to a caregiver so that the caregiver may relive the excess pressure from particular parts by suitably repositioning the patient. However, in generally, such devices are expensive and do not, by themselves, absorb or relieve pressure. For example, it would be rather expensive to change a sock having an array of pressure sensors on a daily basis. Furthermore, there may be problems with machine washing and/or autoclaving, as the connection (e.g., a cable) from the sensor to the electronics may not be adequately protected. Moreover, such devices technologies fail to utilize pressure relieving and shock absorbing areas of the patient's body that could otherwise be used. Furthermore, the dimensions of sensor array devices and spatial constraints for placing these arrays in proximity to a certain body part limit the available locations for placement of such devices. For example, while it may be suitable to use such devices on a mattress or a sheet, it may not work in a shoe or a sock because of the limited space available for placing the sensor without chaffing the user's foot.

Today the development of acquired PU is still of great concern in hospitalized health care. In the United States, PU are observed in more than 500,000 annual inpatient hospital stays. PU is a painful, incapacitating and potentially fatal complication to routine medical and nursing care. Treatment of pressure ulcers is very costly, and the development of pressure ulcers can be prevented by integrating dedicated use of evidence-based best nursing practice. In the United Kingdom alone up to an estimated English Pound.2.1 billion are used annually to treat pressure ulcers—this corresponds to 4% of the National Health Service budget. In addition to the increased cost, the length of the hospital stay will be prolonged and patient recovery will be delayed as well. PU normally results from long periods with continuous pressure and shear induced to the skin and underlying soft and muscle tissue, and bony prominences. High risk patients are elderly people, stroke patients, people with diabetes, individuals with dementia, persons who use wheelchairs or are bedbound, and any patient with reduced mobility.

Often the prevention and treatment of PU are performed unsystematic and based on clinical experience of the individual health care provider. Predictive models have the potential to improve the management and prevention of PU. We have previously shown in a different medical domain how predictive models that fusing of information from different modalities could potentially help preventing serious disease. Several risk scores assessing the patient's risk of developing PU have been proposed and used in medical care such as the Braden, Waterlow and Norton scale. However, the predictive values of these risk-scales have shown low to modest accuracy and are not used in combination with sensor mattress.

SUMMARY

The embodiments herein relate to a system comprising a resting device for resting a patient, wherein the system is configured to collect information from the patient via the resting device over time and construct a user profile of the patient who is laying on the resting device, furthermore, the resting device comprises a patient application recognition algorithm to detect changes in the user profile of the patient and thereby predict in advance any potential adverse health effect on the patient. The resting device could comprise a wireless sensor with a built-in pressure sensor. The system is configured to provide an automatic feedback from the patient application recognition algorithm to the patient using light, words, text message or alarm. The system is further configured to provide the automatic feed to a professional health care giver. The resting device comprises a mattress or chair.

In further embodiments herein, the system is configured to undertake risk stratification, predication and detection. The resting device comprises a contact surface for contacting the patient and has one or more voxels or areas that are able to transmit pressure using a material. The material that transmits pressure is also shock-absorbing and pressure relieving. The resting device comprises a pressure detection device over voxels or areas, wherein the pressure detection device comprises the built-in pressure sensor that comprises a force resistant film or a piezo-electric sensitive material. The built-in pressure sensor is combined with or part of an identification chip or a radio frequency identification chip that is configured to send information to a receiver. If one sends radio signal to the chip, the chip can detect the information, get activated, and send the information that the chip has measured back to the receiver.

In an embodiment, a device includes five components: (1) pressure-relieving embodiment e.g. a mattress (2) with one or more sensors (3) a microchip containing a pattern recognition algorithm/model a (4) mobile application for care monitoring and (5) a patient feedback system using one or more of audio, visual, audiovisual or haptic signal that prompt the patient to perform a preventing action e.g. self-turning. The combination of these five components will enable the present invention to predict adverse events in bedridden people and in due time warn the professional personal or the patient. Thus, preventing a serious incident.

In an embodiment, a device includes a substrate having a contact surface for contacting a user, one or more sacs associated with the contact surface of the substrate, and one or more sensors in communication with the one or more sacs, the one or more sensors adapted to measure changes in pressure in the one or more sacs. The sacs contain a material configured to transmit pressure. The material is further configured to be shock-absorbing and pressure-relieving such that the material is displaceable by an action of the user contacting the contact surface causing the pressure in the material to be redistributed. The one or more sensors adapted to measure changes in pressure in the one or more sacs.

In an embodiment, a device includes a substrate having a contact surface for contacting a user, one or more sacs associated with the contact surface of the substrate, and one or more sensors in communication with the one or more sacs, the one or more sensors adapted to measure changes in pressure in the one or more sacs. The sacs contain a material configured to transmit pressure. The material is further configured to be shock-absorbing and pressure-relieving such that the material is displaceable by an action of the user contacting the contact surface causing the pressure in the material to be redistributed. Changes in pressure in the one or more sacs are measured using one or more sensors in communication with the one or more sacs.

In an embodiment, a system includes (i) a device having a substrate having a contact surface for contacting a user and one or more material filled sacs associated with the contact surface of the substrate, (ii) a controller configured to transmit and/or receive radio frequency signals to and from the one or more sensors corresponding to the measured changes in pressure, and (iii) a user feedback device in communication with the controller. a substrate having a contact surface for contacting a user, one or more sacs associated with the contact surface of the substrate, and one or more sensors in communication with the one or more sacs, the one or more sensors adapted to measure changes in pressure in the one or more sacs. The sacs contain a material configured to transmit pressure. The material is further configured to be shock-absorbing and pressure-relieving such that the material is displaceable by an action of the user contacting the contact surface causing the pressure in the material to be redistributed. The user feedback device configured to provide an indication to a user based on the measured changes in pressure. Changes in pressure in the one or more material filled sacs are measured using one or more sensors in communication with the one or more material filled sacs.

In an embodiment, a method includes measuring pressure exerted by a portion of a subject's body on one or more sacs associated with a substrate having a contact surface for contacting with the portion of the subject's body to provide pressure information and transmitting the pressure information to a receiving station. The pressure information indicates, using one or more of audio, visual, audiovisual or haptic signal.

A pressure-relieving embodiment, example giving a mattress, a seat, a pillow or a shoe sole, but not limited to these examples, with integrated temperature and pressure mapping sensors, that synchronizes data with a screening and pattern recognition algorithm. This algorithm assesses a PU risk score based on individual patient parameters and a long-term real-time recording of how pressure and temperature have been distributed in the patient's body. In an embodiment, a device includes a substrate having a contact surface for contacting a user, one or more sacs associated with the contact surface of the substrate and containing a matrix of voxels. One or more sensors are incorporated in one or more voxels, the one or more sensors adapted to measure changes in the one or more voxels. The material is configured to be shock-absorbing and pressure-relieving such that the material is deformable by an action of the user contacting the contact surface causing the pressure in the material to be redistributed.

In an embodiment, a system includes (i) a device having a substrate having a contact surface for contacting a user and one or more material filled sacs containing a matrix of voxels and associated with the contact surface of the substrate, (ii) a controller configured to transmit and/or receive radio frequency signals to and from the one or more sensors corresponding to the measured changes in the voxels, and (iii) a user feedback device in communication with the controller. A substrate having a contact surface for contacting a user, one or more sacs associated with the contact surface of the substrate, and one or more sensors in communication with the one or more voxels, the one or more sensors adapted to measure changes in voxels in the one or more sacs. The voxels contain a material configured to transmit pressure, temperature or humidity etc. The material is further configured to be shock-absorbing and pressure-relieving such that the material is deformable by an action of the user contacting the contact surface causing the pressure in the material to be deformed. The user feedback device configured to provide an indication to a user based on the measured changes in one or more sensors.

In an embodiment, a system includes a patient wearable, example giving a wrist band or an adhesive band placed on the skin, but not limited to these examples, including one or several of the following functions (i) one or more RFID tags that are used to 3D location of the wearable (ii) One or sensors e.g. movement, heart-rate, temperature etc. and (iii) a controller configured to transmit and/or receive radio frequency signals to and from the one or more sensors corresponding to the measured changes, and (iiii) a user feedback device in communication with the controller, and (iiiii) patient ID. The patient wearable is to be paired with the patient and the patient device and patient station.

In an embodiment, a method includes measuring pressure, temperature or humidity exerted by a portion of a subject's body on one or more sacs containing a matrix of voxels associated with a substrate having a contact surface for contacting with the portion of the subject's body to provide sensor information's and transmitting the information to a receiving station. The information indicates, using one or more of audio, visual, audiovisual, digital and/or haptic signal to the patient and the users.

In an embodiment, a method for monitoring and predicting of adverse events, using changes in sensor data in conjunction with one or more suitable prior information about the person or his/her behavior and conditions.

BRIEF DESCRIPTION OF DRAWINGS

In the present disclosure, reference is made to the accompanying drawings, which form a part hereof. In the drawings, similar symbols typically identify similar components, unless context dictates otherwise. Various embodiments described in the detailed description, drawings, and claims are illustrative and not meant to be limiting. Other embodiments may be used, and other changes may be made, without departing from the spirit or scope of the subject matter presented herein. It will be understood that the aspects of the present disclosure, as generally described herein, and illustrated in the Figures, can be arranged, substituted, combined, separated, and designed in a wide variety of different configurations, all of which are contemplated herein.

DETAILED DESCRIPTION

Figure 1A:
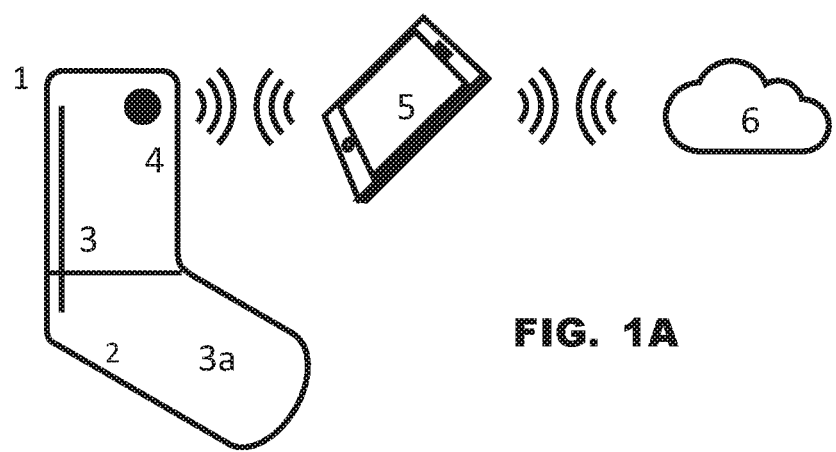
FIGS. 1a and 1b depict embodiments of a pressure monitoring device incorporated in a sock, in accordance with the principles and aspects of the present disclosure.

Before the present methods and systems are described, it is to be understood that this disclosure is not limited to the particular processes, methods and devices described herein, as these may vary. It is also to be understood that the terminology used herein is for the purpose of describing the particular versions or embodiments only and is not intended to limit the scope of the present disclosure which will be limited only by the appended claims. Unless otherwise defined, all technical and scientific terms used herein have the same meanings as commonly understood by one of ordinary skill in the art.

It must also be noted that as used herein and in the appended claims, the singular forms "a", "an", and "the" include plural reference unless the context clearly dictates otherwise. Thus, for example, reference to a "sensor" is a reference to one or more sensors and equivalents thereof known to those skilled in the art, and so forth. Nothing in this disclosure is to be construed as an admission that the embodiments described in this disclosure are not entitled to antedate such disclosure by virtue of prior invention. As used in this document, the term "comprising" means "including, but not limited to."

Furthermore, reference to "prior information" is a reference to one or more measurement(s), or observations about a person. Prior information could be observational data about hospitalized patient eating pattern, mobility level, physical activity level, mental activity level, state of consciousness, oedema, laboratory analysis age, gender, BMI or comorbidities.

Disclosed herein are devices, methods and systems for monitoring and detection of pressure or temperature on a part of a body of a user. In an embodiment, a device includes a substrate having a contact surface for contacting a user, one or more sacs associated with the contact surface of the substrate, and one or more sensors in communication with the one or more sacs, the one or more sensors adapted to measure changes in pressure in the one or more sacs. The sacs contain a material, such as a material, configured to transmit pressure. The material is further configured to be shock-absorbing and pressure-relieving such that the material is displaceable by an action of the user contacting the contact surface causing the pressure in the material to be redistributed. The material could be further subdivided into voxels to minimize shear stress between the patient skin and the system.

Disclosed herein are methods for monitoring and predicting of adverse events, using changes in sensor data in conjunction with one or more suitable prior information about the person or his/hers behavior and conditions. Embodiments disclosed herein also describe devices and systems for implementing those methods and methods of use of such devices and systems. In various embodiments, devices and systems described herein may be used as part of other systems for prophylaxis, or treatment and/or alleviation of symptoms of a disease or a physiological condition In many embodiments, sensor data may be gathered for minutes, hours, days or even months prior to induction of the physiological event. As such, incidence of various features and patterns extracted from the sensor data may be correlated with the particular physiological event being induced based on the analysis being performed.

In many embodiments the prior information's and sensor data collected over hours/days/months is used in the pattern recognition algorithm to construct a user specific profile. As such, the user profile may be generated by combining the sensor data from various pieces of personal furniture e.g. a chair, a bed or pressure relieving aids.

In one embodiment the pattern recognition algorithm may detect changes to the user profile over hours/days/months in e.g. body temperature, weight or movement. And based on these changes the algorithm will calculate a prediction of PU in minutes.

In one embodiment the pattern recognition algorithm may detect changes to the user profile over hours/days/months in e.g. body temperature, weight or movement. And based on these changes the algorithm will predict an upcoming advance effect e.g. an increases in body weight increases the risk for kidney and heart disease. While a decreases body weight over time (5% weight loss in 1 week) and decreases in body movement and increases in body temperature are signs of dehydration.

As used herein, the term "sensor" refers to a device that measures a physical quantity and converts it into a signal, which can be read by an observer or an instrument. In an embodiment, a pressure sensor may be a device for measuring a pressure and converting it into an electrical signal that can be read using an electronic instrument. In such embodiment, a change in pressure results in an electrical signal or a change in an electrical signal that is correlated with the change in pressure, thereby providing a measure of the change in pressure. The pressure measured by a pressure sensor may be absolute pressure or relative pressure, e.g., pressure relative to atmospheric pressure.

Likewise, a temperature sensor may convert a temperature or a change in temperature into an electrical signal and a humidity sensor may convert humidity or a change in humidity into an electrical signal. The humidity measured by a humidity sensor may be absolute humidity or relative humidity. In various embodiments, a sensor may need to be calibrated to provide a meaningful measure. In some embodiments, a sensor may not convert a measurement into an electrical signal.

Examples of pressure sensors include, but are not limited to, (i) strain gauges wherein stretching of a lead wire leads to a measurable change in resistance of the lead wire; (ii) piezo-resistive sensors wherein resistance of the sensor material is sensitive to deformations and displacements; (iii) capacitive sensors wherein capacity of the sensor is measurably changed because a deformation causes a change in the distance between the plates and/or the overlapping area of the plates (iiii) Force-resistant sensor wherein the resistance of the sensor is measureable changed because a deformation causes a change in force; and the like.

As used herein, the term "voxels" is one or more equal or different three-dimensional volumes containing a "material" which can be a gas, a liquid, a gel, or a pressure-absorbing solid, e.g., foam. Examples of material include, but are not limited to, ethylene vinyl acetate, rubber, silicone rubber, Polyurethane rubber (PUR), neoprene, or air. One embodiment of the "material" is a "fluidic material." Terms "sac," "material sac", or "material filled sac," or "sac filled with material" are used interchangeably and refer to a cover, a cavity filled with a material such as a gas, a liquid, a gel, or a pressure absorbing solid. Embodiments of "sac," "material sac", or "material filled sac," or "sac filled with material" include "material sac," or "material filled sac," or "sac filled with material." The material, such as fluid material, filled sac can be made from a textile fabric material such as, for example, nylon, spandex, silk, wool, cotton, polyester, and the like, or a combination thereof. In other embodiments, the material filled sac can be made from a pliable material such as, for example, rubber, plastic, silicone, neoprene and the like, or any combination thereof.

In some embodiments, the material in the material filled sac is chosen such that excess pressure at a localized area of the sac is redistributed throughout the sac by displacement of the material, thereby relieving the pressure from the localized area. In some embodiments, the material in the material filled sac is chosen such that excess pressure at a localized area of the sac is redistributed throughout the sac by displacement of the material, thereby relieving the pressure from the localized area. Furthermore, such a sac filled with a material, such as a fluid material, enables absorption and dissipation of sudden changes in pressure, thereby acting as a shock-absorber. As such, a sac filled with a material described herein can act as a pressure-relieving and shock-absorbing device for a user.

In some embodiments, a plurality of material filled sacs in material conducting communication with each other to form a network may be used. In some embodiments, independently sacs and voxels can be placed in matrix and thereby minimizing shear stress e.g. when the patient moves in the bed. The material in such a network of material filled sacs may redistribute pressure from a small localized area over a larger area, thereby relieving excess localized pressure. Furthermore, such a network also enables absorption and dissipation of sudden changes in pressure, thereby acting as shock-absorber. As such, a network of sacs filled with a material described herein can act as a pressure-relieving and shock-absorbing device for a user.

As used herein, the term "user" refers to a subject, human or animal, that uses the device or system disclosed herein. A user may be a person at risk for pressure ulcers such as, for example, a bed-ridden subject, a patient with neuropathy, a wheel-chair bound person, and the like. In some embodiments, a user may be a subject suffering from pressure ulcers.

Our pattern recognition algorithm is capable of integrating patient information both real-time information and history information to personalize diagnosis of PU risk and keeps a long-term record of pressure changes and temperature data that continuously inform the algorithm regarding the real-time risk level of each individual patient. The diagnosis information provided by our solution (i) is continuously up to date, (ii) is sensitive to aggravation of risk factors (such as temperature increases), (iii) can be accessed by healthcare professionals in their current electronic patient record systems and (iv) enables the deployment of PU prevention strategies when they are most needed, reducing inefficiencies of routine medical and nursing care. Our approach not only increases the quality of life and independence of bedridden patients, but also reduces the costs.

In one embodiment, the pressure relieving, and sensing mattress will be a two-dimensional array of around 200 individually working sensors built into the mattress structure, installable on a normal bed. The sensors will be connected wirelessly, which makes them more prone to resist the normal hospital use, addressing one of the barriers identified in competing products. Each sensor is currently composed of a pressure change measurement unit and a RFID tag or NFC tag. Each tag is capable of measuring temperature, collect the pressure data and communicate wirelessly all the information to a local storage unit. This collected data is continuously transmitted to our ICT backbone for analysis, using a local wireless connection.

The pattern recognition algorithm combines multiples sources of data which contribute to more accurate and robust evaluations and prediction. Our algorithm combines data points from (i) the local electronic patient record system (e.g. BMI, age, edemas), (ii) the mattress continuous real time data, and (iii) healthcare professionals' input using an improved risk measurement scale, based on the Braden or other scales (care professional can choose which one s/he prefers). The result of these multiple data points allowed us to vastly improve the risk stratification and enables prediction of adverse effect(s). Instead of classifying patients as low- or high-risk, our system predicts the risk evolution rate for each individual patient and alerts when it is time to implement a preventive measure. Also, by mapping and analyzing the distribution of the mattress pressures, we can determine the laying orientation of each patient, as well as detect s/he has moved. This is important because a patient that switches sides when lying in a bed is redistributing/alleviating the location of the pressures and the algorithm reflects that change by readjusting the risk scores of each body part. Competing technologies require the nurse to manually reset a timer along with each postural change, while our solution will intelligently determine the best time frame to implement a personalized postural change, suggesting which body areas should be protected from pressure to alleviate the risk.

The smartphone app will communicate with the algorithm to enrich the care experience. The caretaker's UI lets healthcare professionals monitor multiple patients, fill in the improved risk measurement scale for each patient, see a schedule of intelligently predicted postural changes to be performed, and receive notifications when patients reach high risk assessments.

Figure 1B:
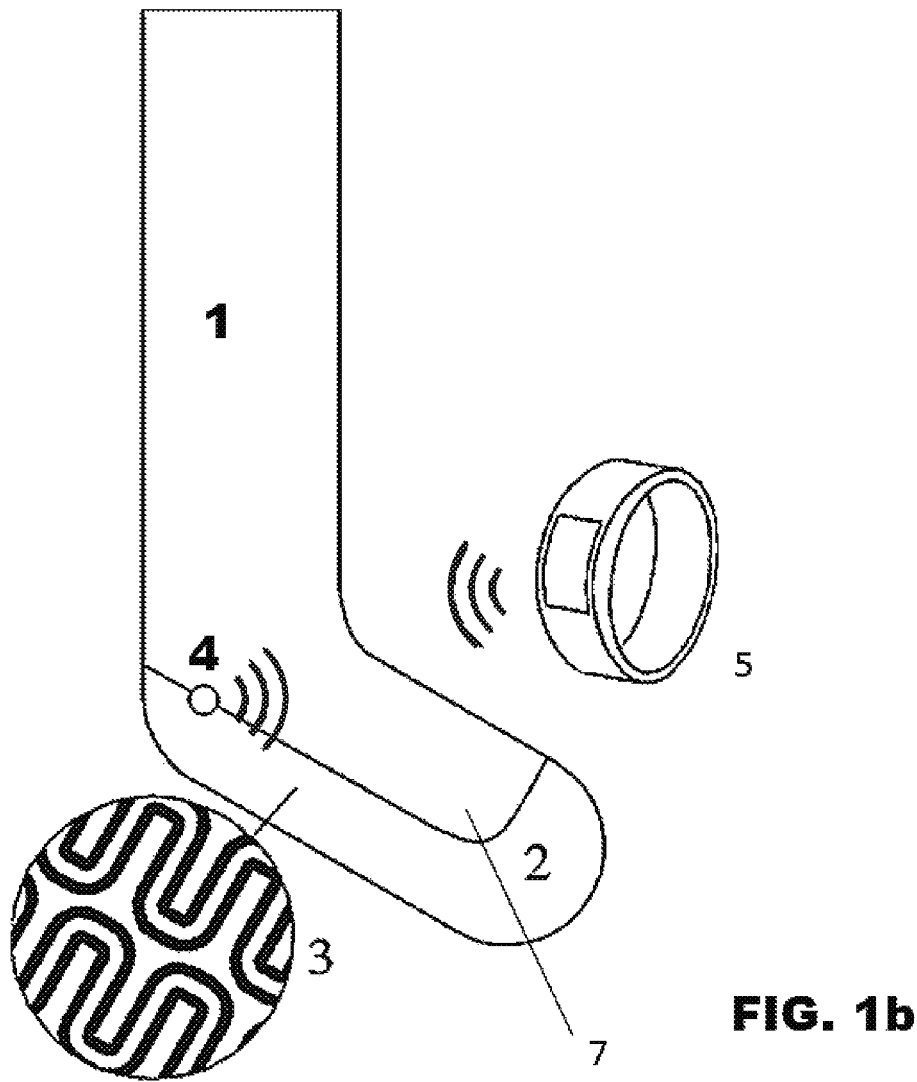

FIGS. 1a and 1b depict embodiment of a pressure monitoring device incorporated in a sock, in accordance with the principles and aspects of the present disclosure. Size of the sock 1 is adapted to the individual user, so it fits comfortably. A pillow-like region forms the substrate 2 and surrounds the underside and the front part of the foot of a user. FIG. 1a shows material filled sacs 3 are disposed in the pillow-like substrate and are configured to transmit the changes to various internal and external factors (e.g., pressure, temperature, humidity and the like) to one or more sensors 4 disposed on the substrate. FIG. 1b is an embodiment wherein the material is a material in material filled sacs 3.

In some embodiments, the substrate 2 is made of thin, flexible, resilient and elastic textile product. Examples of materials that may be used for making substrate include, but are not limited to, nylon, spandex, silk, wool, cotton, polyester, and the like, or a combination thereof. The contact surface of substrate 2 (the contact surface is shown by numeral 7 in FIG. 1b) that engages or comes in contact with the user's foot. Suitable permeability for water vapour and bacteriostatic properties are desirable for the material of the contact surface so as to reduce risk of unwanted infections and for user comfort. Material of contact surface 6 can be natural or synthetic fibres.

Associated with contact surface of substrate is disposed one or more material filled sacs 3 configured such that the material, which could a material, is displaceable between different sacs by an action, e.g. movement of the foot, of the user contacting the contact surface. Such configuration allows for material pressure in the one or more sacs to be redistributed so as to dissipate and relieve excess pressure from a localized portion of a user's body in contact with contact surface.

In various embodiments, material filled sacs 3 can be secured on portions of substrate by means of thermoweld, bonding, molding, laminating, sewing or any other suitable mechanism. In an embodiment, material filled sacs 3 have a meandering pattern. In some embodiments, material filled sacs 3 may be made of silicone, or similar compressible material that is capable of redistributing pressure. In an embodiment, a surface of the material filled sacs coincides with the contact surface.

One or more sensors 4 may be disposed in communication with one or more material filled sacs 3. The sensors 4 may include, for example, pressure sensors, temperature sensors, humidity sensors, blood pressure sensors, and the like. In one embodiment, one or more pressure sensors are disposed and secured inside one of material filled sacs 3. In another embodiment, one or more pressure sensors are disposed and secured on an outer surface of one of material filled sacs 3.

In yet another embodiment, one or more pressure sensors are associated with contact surface of substrate.

In some embodiments, one or more sensors 4 are connected to a transmitter or include a transmitter that can transmit the data measured by one or more sensors 4 from the measurement area to a remote receiver 5. Numeral 4 in the figures refer to sensor or the combination of sensor and transmitter. In various embodiments, the transmitter may use communication technologies such as, for example, Radio Frequency communication (RF), Near Field Communication (NFC), Bluetooth, Bluetooth low energy (BLE), and the like.

In an embodiment, the transmitter is an RF transmitter. RF transmitters are widely used for uniquely identifying objects using radio frequency electromagnetic signals. Examples of uses of RF transmitter include, but are not limited to, inventory control, theft protection, monitoring tires pressure in cars, and the like. Typical RF transmitters use an RF Identifier (RFID) which consists of transmitter (tag) for transmitting a unique identifier and other data to RF Readers, which are configured to receive and decode data transmitted by the RFID. The tag is typically composed of an antenna and a circuit to control a microchip. In some embodiments, the tag's microchip and antenna may both be used for the measurement of pressure. An RF tag may be a passive tag or an active tag. A passive tag has no internal source of energy and therefore, may not require any maintenance. A passive RFID tag is activated only when sending a specific radio signal. At such time the tag "wakes up" and transmits a unique ID number and a characteristic measurable resistance which depends on the pressure of the material it is attached to.

In various embodiments, the RF transmitter may be disposed at a location where it is not obstructive to the user and does not create pressure points. For example, the RF transmitter may be glued to a sole or sewn into a sock. In some embodiments, remote receiver 5 may be, for example, a bracelet, a mobile phone, remote control or the like. Remote receiver 5, in some embodiments, may be configured to provide a feedback to the user and/or a caregiver attending to the user. The feedback system can be embodied with, e.g., colored light, to indicate when a foot is subjected to undesirable stresses. The remote receiver 5 is in contact with other remote receivers 5 and connected wirelessly via a shared server 6.

Figure 10:
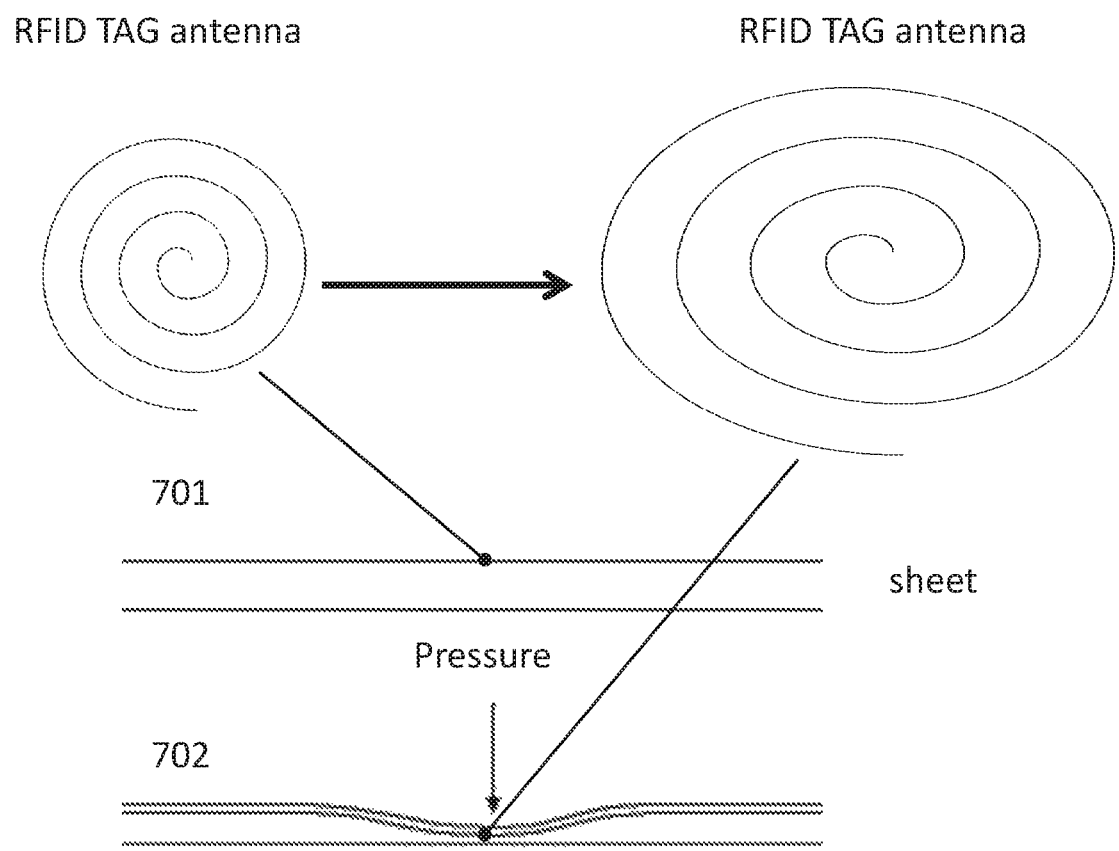
FIG. 10 depicts an embodiment with a radio frequency transmitter is also used a pressure sensor, in accordance with the principles and aspects of the present disclosure.

In various embodiments, a RF transmitter itself may act as a pressure sensor a described elsewhere herein (in reference to FIG. 10). In such embodiments, the RF transmitter may be placed directly at the measuring area, e.g. at one of material filled sacs 3 as a direct pressure sensor, or in proximity as an indirect pressure sensor where the pressure signal from one area is being transmitted to the sensor via one or more other areas.

In various embodiments, the system is composed of two separate devices. A force sensitive resistor film and a sensor TAG e.g. SL900A UHF RFID sensor TAG from AMS embedded within a single flexible inlay. The TAG and antenna may be printed/mounted with e.g. glue directly on sensitive resistor flexible film or maybe separate from the film with a non-conductive foil. The sensor TAG is composed of a microcontroller with built in NFC capabilities, built-in temperature sensor and an interface for external sensors. The pressure sensor e.g. the force sensitive resistor film can be seen as a variable resistor. When force is applied the resistance changes. Because of this, the interface to the microcontroller is a simple voltage divider.

In one embodiment material filled sacs 3 form a tree-like structure whereby different sacs are in material conducting communication with each other via the branches so that pressure changes can be transferred from a material filled sac in one area to one or more material filled sacs in another area via the branches. In some embodiments, material filled sacs 3 may be filled using a movable liquid or gel which, in addition to transferring the pressure changes, can also massage and support the blood circulation during operation. Such configuration provides the advantage that any excess pressure affecting the contact surface is distributed over a larger area, thereby minimizing its deleterious effects. The material in material filled sacs 3 can move and can be used to measure the pressure or change in pressure using one of or more sensors 4. In embodiments with a transmitter, and a remote receiver, measurements of pressure or change in pressure are further transmitted to the remote receiver via the transmitter.

In one embodiment material filled sacs may consist of different material which is optimized for different part of the body.

Figure 2A:
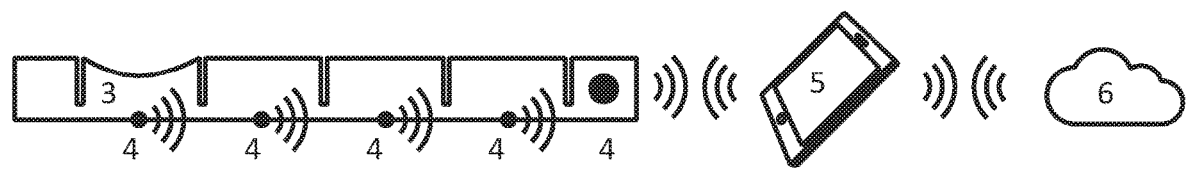
FIGS. 2a and 2b depict illustrative schematics of response of a device subjected to a local compressive load, in accordance with the principles and aspects of the present disclosure.

FIG. 2a depicts an illustrative schematic of response of a device subjected to a local compressive load, in accordance with the principles and aspects of the present disclosure. The sac is subdivided into a matrix of voxels. FIG. 2 depicts suppression by a local compressive load of one of these voxels. And FIG. 2 depicts schematically depicts how the pressure changes (both static and dynamic changes) in the material in material filled sac 3 propagate to one or more sensors 4. The sensor transmits data to a remote receiver 5, which may be in contact with other remote receivers 4 and connected wirelessly via a shared server 6.

Figure 2B:
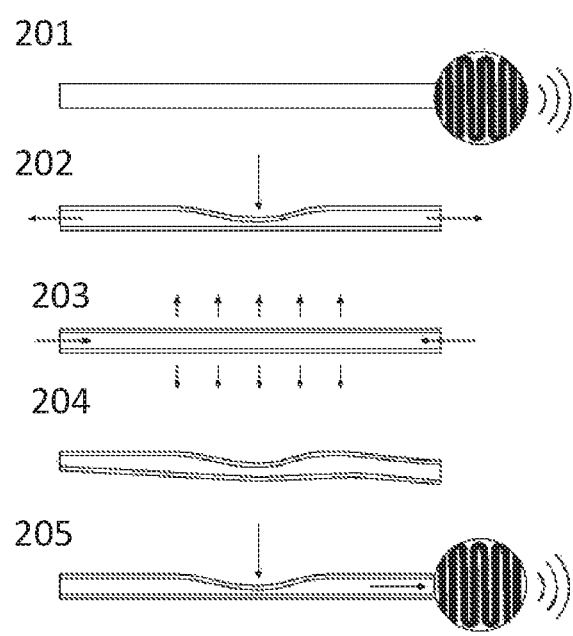

FIG. 2b depicts an illustrative schematic of response of a device subjected to a local compressive load, in accordance with the principles and aspects of the present disclosure. 201 depicts a schematic drawing of material filled sac 3 is shown. 202 schematically depicts the effect of subjecting material filled sac 3 to a local compressive load. 203 schematically depicts how the local compressive load is quickly eliminated by the pressure being dispersed to the entire material. 204 schematically depicts that the material used to fill material filled sac 3 is resilient and can expand if necessary. 205 schematically depicts how the pressure changes (both static and dynamic changes) in the material in material filled sacs propagate to one or more sensors 4.

Figure 3A:
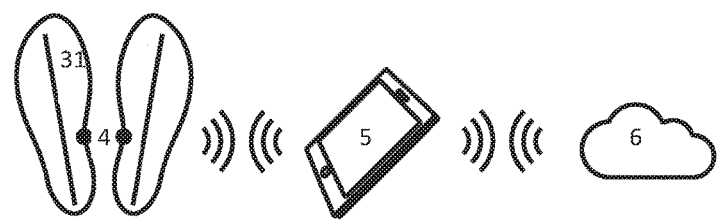
FIGS. 3a and 3b depict embodiments of a pressure monitoring device incorporated in a shoe-sole that is controlled using a smartphone, in accordance with the principles and aspects of the present disclosure.

FIG. 3a depicts an embodiment of a pressure monitoring device incorporated in a shoe-sole is controlled using a smartphone, in accordance with the principles and aspects of the present disclosure. The shoe sole 31 acts as the substrate. Sensors 4 are placed on the underside of the shoe sole. Numeral 5 depicts an example of a remote receiver and numeral 6 depicts a collecting server and/or cloud service.

Figure 3B:
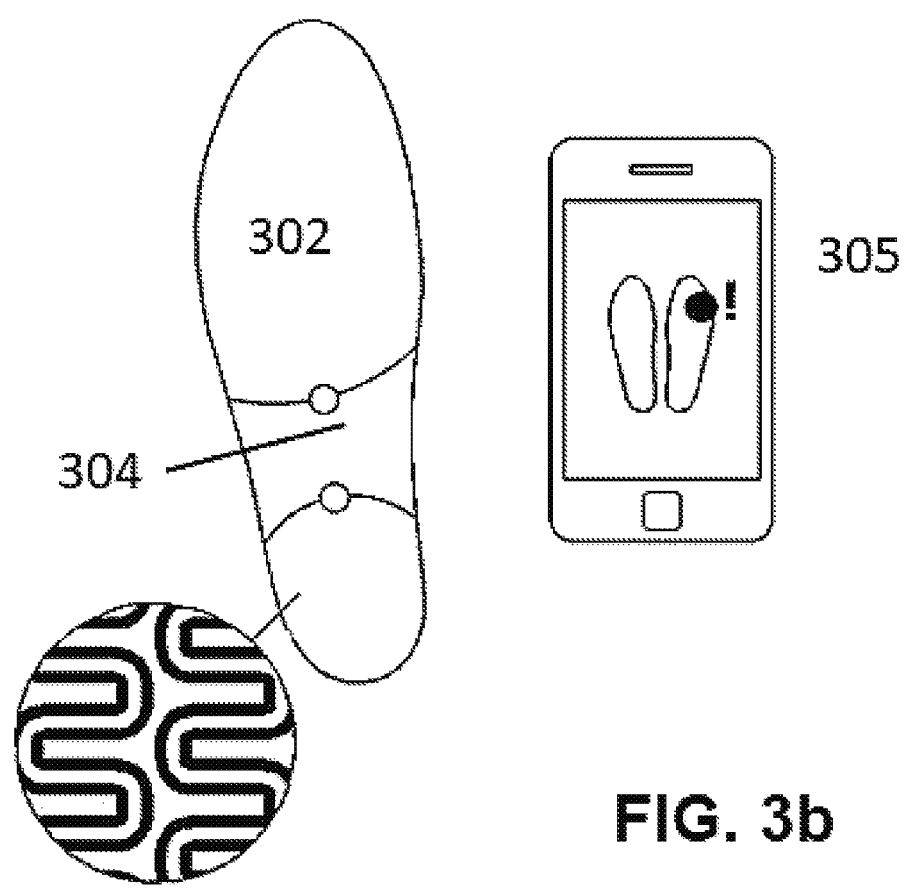

FIG. 3b depicts an embodiment of a pressure monitoring device incorporated in a shoe-sole is controlled using a smartphone, in accordance with the principles and aspects of the present disclosure. The shoe sole 302 acts as the substrate. Sensors 304 are placed on the underside of the shoe sole. Numeral 305 schematically depicts an example of user interface for a remote receiver in the form of a smart-phone.

In various other embodiments, substrate may be an article in contact with a user's body. Examples of substrates include, but are not limited to, sheets, mattresses, in-soles of shoes, socks, gloves, seat cushions, seat covers, and the like. A skilled artisan will be able to contemplate other embodiments of pressure monitoring devices in accordance with various principles and aspects of the present disclosure.

Figure 4A:
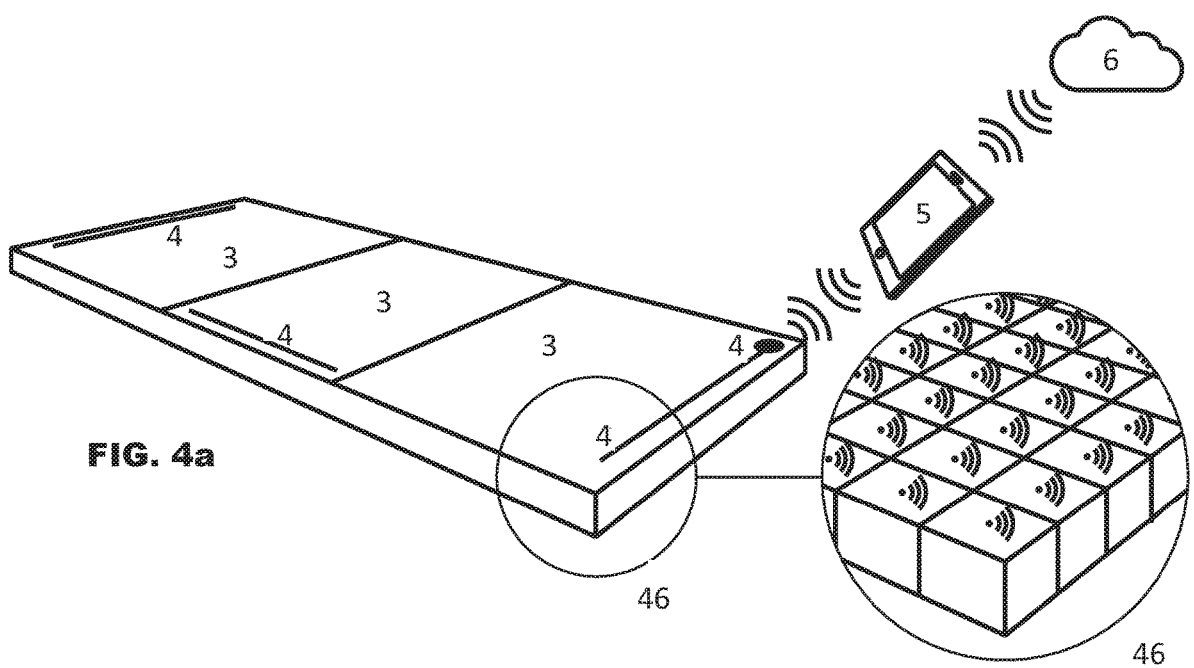
FIGS. 4a and 4b depict embodiments of a pressure-monitoring device incorporated in mattress, in accordance with the principles and aspects of the present disclosure.

For example, FIG. 4a depicts an embodiment of a pressure monitoring device wherein the substrate is a sheet (or a mattress cover). 3 schematically depicts an example of placement of material filled sacs. 4 Numeral depicts different antennas (sensor/transmitter) detecting the 3D location and orientation of the remote receiver 5, which in turn transmits data wirelessly to the cloud 6 which could comprise a shared server. Numeral 46 schematically depicts a matrix of voxels, which each sac is subdivided into, and an example of placement of sensors below/in each voxel. Other components of the pressure monitoring device may be suitably placed by one skilled in the art in accordance with various aspects and principles disclosed herein.

Figure 4B:
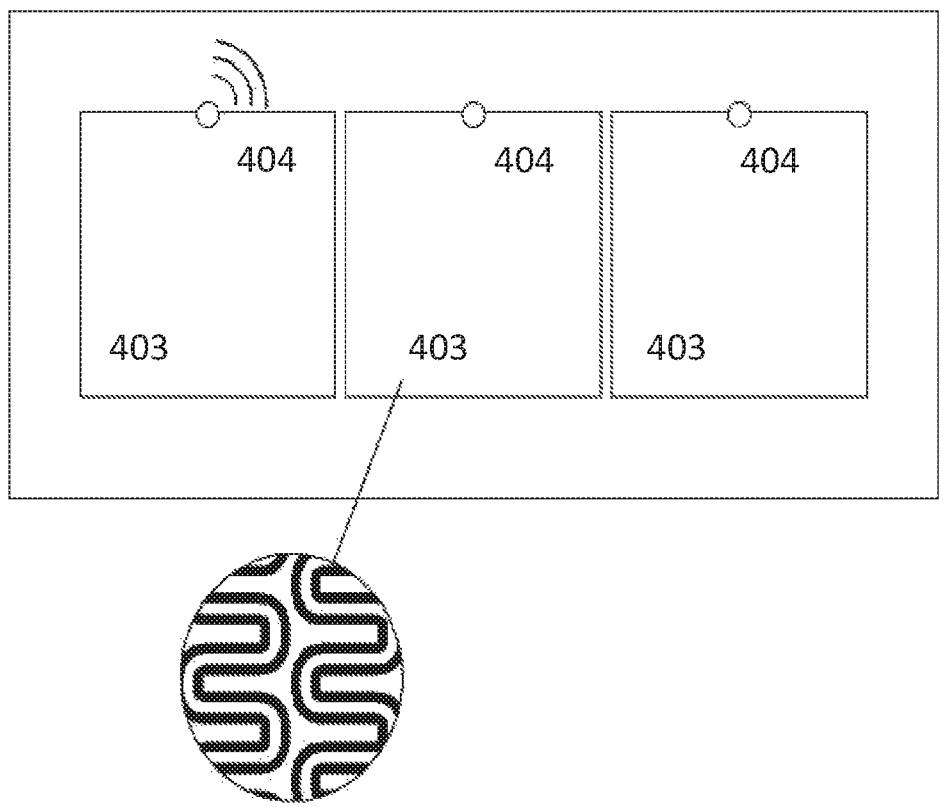

FIG. 4b depicts an embodiment of a pressure monitoring device wherein the substrate is a sheet (or a mattress cover). Numeral 403 is an example of placement of material filled sacs. Numeral 404 schematically depicts an example of placement of sensors. Other components of the pressure monitoring device may be suitably placed by one skilled in the art in accordance with various aspects and principles disclosed herein.

One advantage of such a device is that the sensors and associated electronics may be located visibly, hidden away from the measurement area, or can be removable. This means that the sensors and associated electronics can be removed, to facilitate cleaning, including the machine-washing of the device.

In one embodiment, a pressure monitoring system may include a device comprising: (i) a substrate having a contact surface for contacting a user; (ii) one or more material filled sacs associated with the contact surface of the substrate, and (iii) one or more sensors in communication with the one or more material filled sacs. The sacs contain a material configured to transmit pressure. The material is further configured to be shock-absorbing and pressure-relieving such that the material is displaceable by an action of the user contacting the contact surface causing the pressure in the material to be redistributed. The one or more sensors are adapted to measure changes in pressure in the one or more material filled sacs. The one or more sensors are in communication with at least one transmitter adapted to transmit a measurement by the one or more sensors. The system further includes a controller configured to transmit and/or receive signals to and from the one or more sensors corresponding to the measured changes in pressure, and a user feedback device in communication with the controller. The user feedback device is configured to provide an indication to a user based on the measured changes in pressure.

In some embodiments, the at least one transmitter is adapted to transmit wireless signals using technologies such as, for example, Radio Frequency communication (RF), Near Field Communication (NFC), Bluetooth, Bluetooth low energy (BLE), and the like. The controller is adapted to transmit and/or receive signals compatible to the transmitter.

A receiver containing electronics and user feedback device as display, speakers, and/or an LED light need not be placed on the substrate. These can be placed anywhere on the user interface device or used in the immediate vicinity of the substrate, thereby avoiding placement of hard materials at sites that have high risk of forming pressure ulcers. Additionally, the signal and the power cable may be completely avoided by the sensors and electronics to wirelessly transmit data from the recorded measurement range to the remote receiver, which can be placed at a place on the device or in the vicinity of the latter.

In various embodiments, the user feedback device may be configured to provide an indication or an alert to a user and/or a caregiver attending to the user if the pressure information indicates a pressure in excess of a pre-determined threshold and/or for duration longer than a pre-determined period of time. The threshold pressure and period of time may be determined by the user and/or the caregiver based on factors such as, for example, age, sex, weight, blood pressure, and/or other factors relating to the user that determine the user's risk of contracting pressure ulcers.

Figure 5:
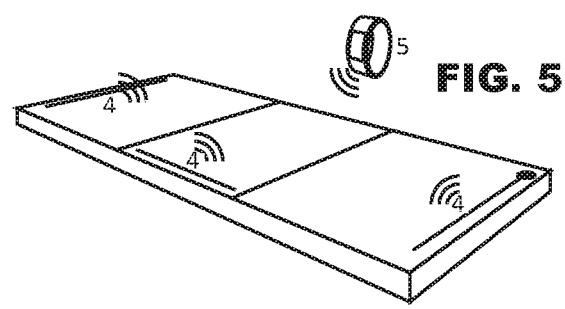
FIG. 5 depicts a patient wristband together with mattress, where the mattress can detect the 3D location and orientation of the wristband.

FIG. 5 depicts a patient wristband 5, which can be detected in 3D orientation and 3D location in relation to the mattress 51 by the build in antennas 4 in the mattress 1.

Figure 6:
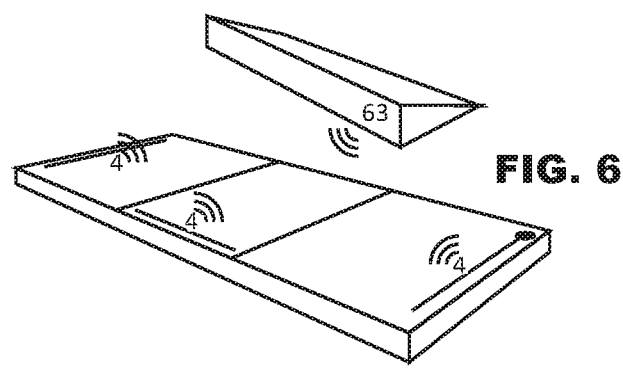
FIG. 6 depicts a pillow or wedge together with a mattress, where the mattress can detect the 3D location and orientation of the pillow or wedge.

FIG. 6 depicts a pillow or wedge 63, which can be detected in 3D orientation and 3D location in relation to the mattress 61 by the build in antennas 4 in the mattress 61. The pillow or wedge has built-in sensors, which are communicating wirelessly with the receiver in the mattress 61.

Figure 7:
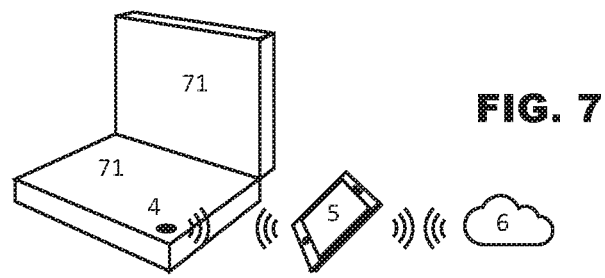
FIG. 7 depicts a seat with a backrest with a cloud service, in accordance with the principles and aspects of the present disclosure.

FIG. 7 depicts a seat and back-rest 71 with build in sensors/transmitter 4 like the mattress in FIG. 4a, able to communicate wirelessly with a smartphone/receiver 5 and further with a cloud service 6.

Figure 8:
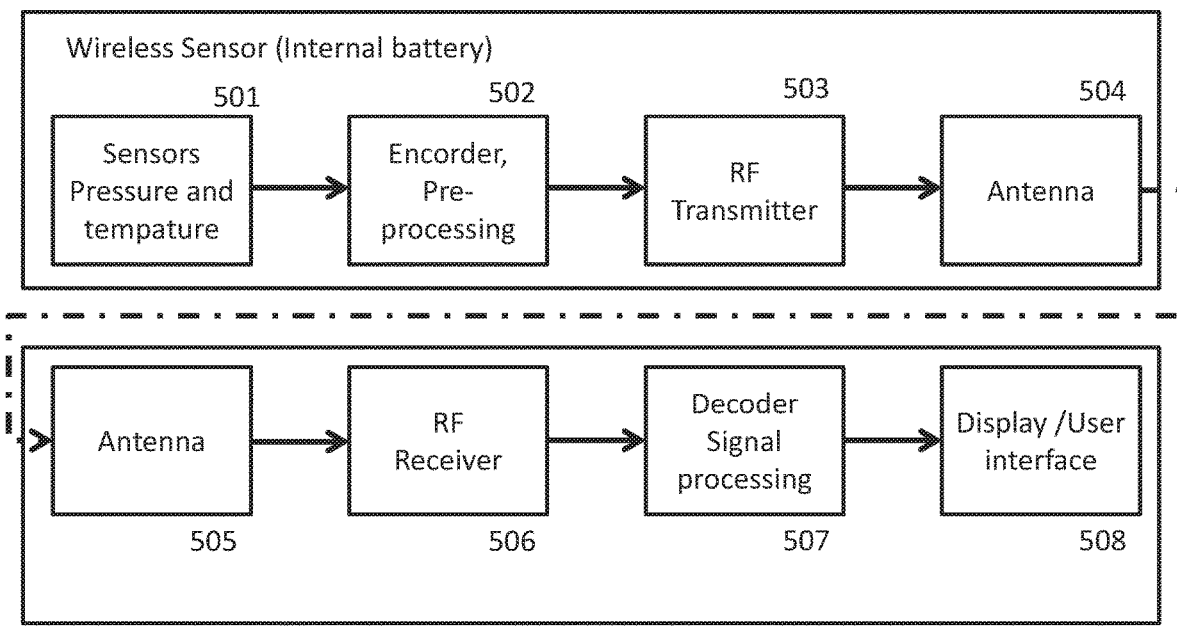
FIG. 8 depicts an embodiment of a wireless pressure monitoring system, in accordance with the principles and aspects of the present disclosure.

FIG. 8 depicts the flow of signals in a wireless pressure monitoring system, in accordance with the principles and aspects of the present disclosure. The embodiment depicted in FIG. 5 includes a temperature sensor to account for pressure changes due to temperature changes. At 501 temperature and pressure data is measured using one or more sensors. This data is encoded and preprocessed at 502 and delivered to the RF transmitter at 503. At 504, the antenna of the RF transmitter transmits pre-processed pressure and temperature data as an RF signal which is received, at 505, by the antenna of the RF receiver. The RF receiver, at 506, delivers the signal to the controller. At 507, the controller decodes the pressure and temperature data, performs additional signal processing (if required) and delivers it to the user feedback device. At 508, the user feedback indicates the temperature and pressure data to the user.

In various embodiments, the controller and the user feedback device may be incorporated in a single device such as, for example, a smartphone, a laptop computer, a tablet computer, a dedicated handheld device, and the like. The user feedback device may indicate a feedback using, for example, audio, audiovisual, visual, or haptic signals.

Various portions of electronics used in the system of the embodiment described with respect to FIG. 8 may be powered using an internal battery. For example, a battery may be disposed in one of the material filled sacs and be connected to the one or more sensors and the RF transmitter. The energy required for preforming the pressure and/or temperature measurements (as well as other measurements where applicable) as well as for encoding and pre-processing the measurement data may be provided by such a battery. Furthermore, such a battery may also provide energy required by the RF transmitter for transmitting the pressure and temperature data (as well as other data where applicable). Such embodiments may provide continuous real-time data from the measurements. However, such embodiments may be limited in time of use by failure of the internal battery which may need to be replaced periodically and may increase the operating costs. In some other embodiments, a connection lead (not shown) may be provided to the sensor and/or the RF transmitter from outside the substrate. This connection lead may be used to provide energy (using a battery or any other source of electricity). In yet other embodiments, the system may be modified to work without an internal battery.

Figure 9:
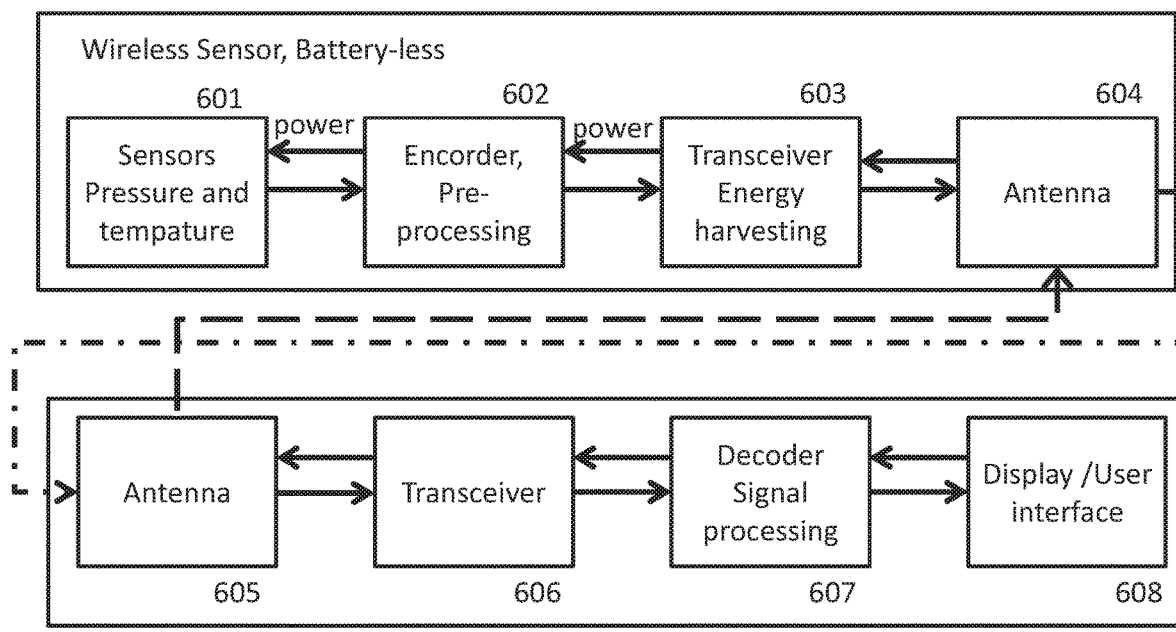
FIG. 9 depicts an embodiment of a battery-less wireless pressure monitoring system, in accordance with the principles and aspects of the present disclosure.

In one embodiment, as depicted in FIG. 9, the system lacks an internal battery used to power the sensors and the RF transmitter. In such an embodiment, the one or more sensors are connected to an RF transceiver which is enabled to harvest energy from a received RF signal. This energy is used to power the sensor(s) to allow the sensor(s) to perform the desired measurements. Alternatively, such an embodiment may use a passive RF tag.

FIG. 9 depicts an embodiment of a battery-less wireless pressure monitoring system, in accordance with the principles and aspects of the present disclosure. At 608, a user or a caregiver requests, through the user feedback device, for pressure and/or temperature data. The request is transmitted through the controller, to the RF transmitter (through 607, 606, 605, and 604, indicated by arrows pointing left). At 603, the RF transceiver harvests energy from the signal it receives and powers the encoder and the sensor(s) (as indicated by the arrows pointing left and labeled power). At 601 temperature and pressure data is measured using one or more sensors. This data is encoded and preprocessed at 602 and delivered to the RF transmitter at 603. At 604, the antenna of the RF transmitter transmits pre-processed pressure and temperature data as an RF signal which is received, at 605, by the antenna of the RF receiver. The RF receiver, at 606, delivers the signal to the controller. At 607, the controller decodes the pressure and temperature data, performs additional signal processing (if required) and delivers it to the user feedback device. At 608, the user feedback indicates the temperature and pressure data to the user.

FIG. 10 depicts an embodiment with a radio frequency transmitter is also used a pressure sensor, in accordance with the principles and aspects of the present disclosure. In an embodiment, a pressure sensor consists of one or more of the passive or active RF tags that can be embedded in a material filled sac for radio communication and for measuring both static and dynamic pressure changes. When load on the material filled sac increases, the antenna embedded in the material filled sac gets stretched resulting in a change in the antenna's detectable complex resistance. This can be used to measure the change in pressure experienced by the material filled sac.

The devices and systems described herein open new possibilities for a person to monitor problem areas on the body continuously in his daily life, which in turn opens up new opportunities for long-term monitoring of chronic wounds.

Figure 11A:
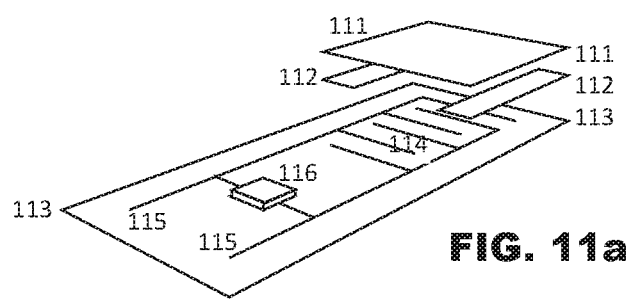
FIGS. 11a and 11b depict schematic drawings of sensors and wireless transmitter.

FIG. 11A depicts schematic drawings of the construction of sensors with wireless transmitter. The upper layer is a resistive polymer 111 glued on space layer(s) 112 and onto the lower layer 113 with electrodes 114 connected to antennas 115 and a transmitter/sensors 116.

Figure 11B:
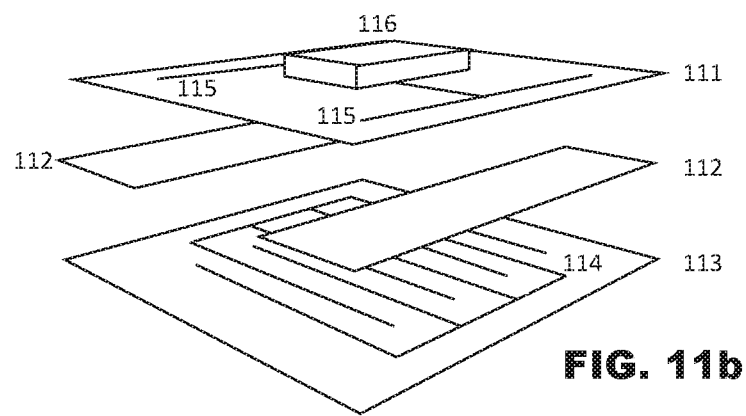

FIG. 11B depicts a variation of 11A with antennas 115 and transmitter/sensors positioned on the upper resistive polymer layer 111.

Figure 12:
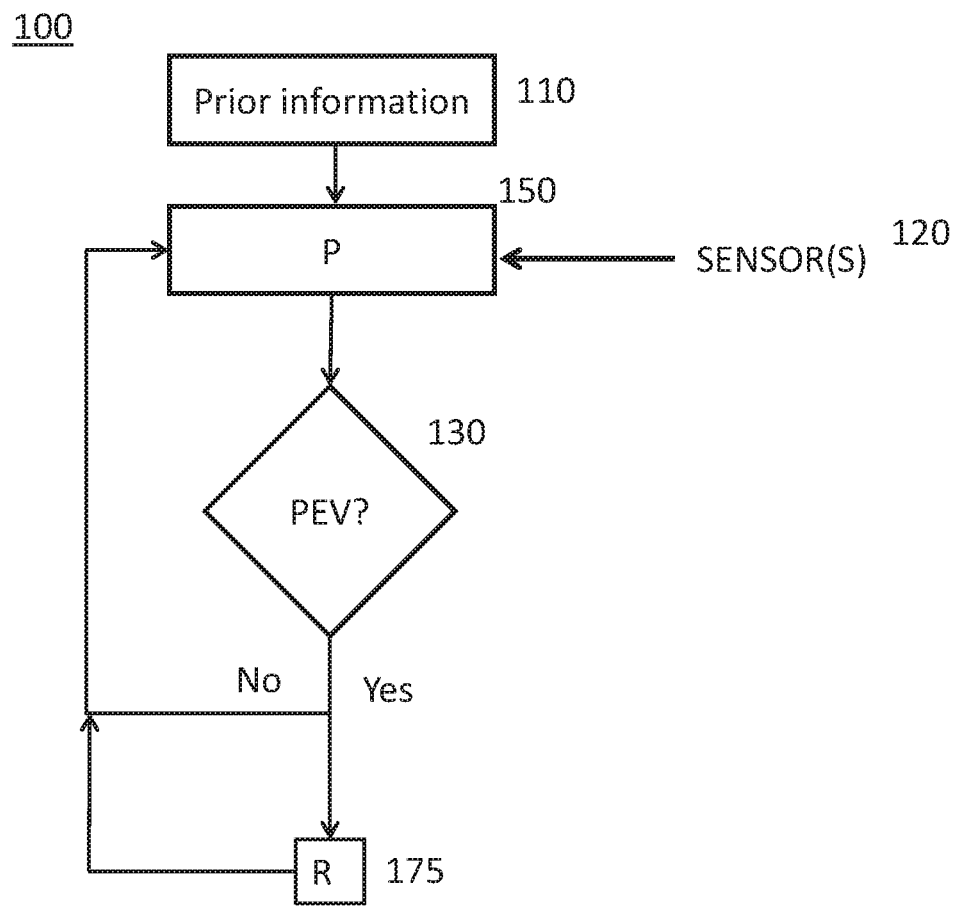
FIG. 12 depicts an illustrative process for a method of monitoring, risk estimating and predicting pressure ulcers using measurements (sensor data) such as from pressure, movement or temperature sensors in combination with one or more prior information about the person.

FIG. 12 depicts an illustrative process for a method of monitoring and predicting a pressure ulcer using sensor data in combination with one or more prior information according to an embodiment. At block 110, prior information of a subject is obtained. The prior information fed to a processor P which, at block 150, analyzes the data based on a pre-determined algorithm. At block 130, processed data is combined (using, e.g., another processor not shown in FIG. 1) with measurements relating to sensor data from one or more sensors gathered at block 120 and analyzed for change in risk of pressure ulcers. This analysis may be fed back to processor P for analysis at block 150. If the change in risk of pressure ulcers is deemed, based on a pre-determined set of criteria, a reaction R is provided at block 175.

Figure 13:
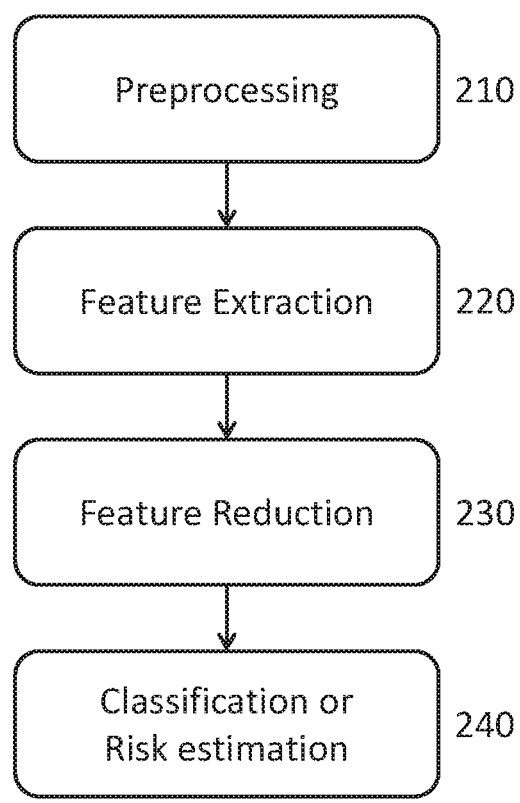
FIG. 13 depicts an illustrative pattern recognition model according to an embodiment.

Sensor data of a subject may be measured using any device or method. For example, in an embodiment, Sensor data of a subject is measured using pressure sensors. FIG. 10 depicts an illustrative pattern recognition model according to an embodiment. In various embodiments, analysis of Sensor data at block 150 may include, for example in FIG. 13, preprocessing at block 210, feature extraction at block 220, feature reduction at block 230, and classification or risk estimation at block 240.

In embodiments where sensor data is measured using a pressure sensor, a signal from the pressure sensor is preprocessed, at block 210, for removal of noise and uninformative information.

Preprocessing of the sensor data from the pressure sensor may be followed by feature extraction, at block 220. Preprocessed data is sent to block 220 to find, preferably, a small number of features that are particularly distinguishing and/or informative for classification and/or risk estimation of pressure ulcer. Features may be mathematical derivative from the sensor data from any interval in obtained data.

Analysis performed on the sensor data at block 220 may, in various embodiments, include, for example, differentiation, averaging, calculation of slope, ratios of instantaneous values, standard deviation, skewness, regression coefficients, slopes of regression ratios, and standardized moment, and so forth. Features extracted from the sensor data may include, for example, median pressure data from particular epoch range prior to an event occur, or the skewness of pressure data particular epoch range prior to an event, and so forth.

Sensor data extracted at block 220 may include a large number of different features may be evaluated for their ability to predict pressure ulcer. Such features may then, be passed down to block 230 to be grouped to form patterns that may be indicative of a pressure ulcer event. At block 230, a ranking algorithm based on e.g. a t-test or ROC may be used, in some embodiments, for eliminating features that do not signify an event prediction.

In some embodiments, the ranking algorithm may calculate an average separability criterion for each feature. Such a criterion may reflect the ability of the classification method to separate the means of any two classes of features in relation to the variance of each class. Subsequently, various features may be correlated with physiological events. Features with lowest separability may be eliminated if correlation with higher ranking features exceeds a threshold. In an embodiment, a correlation threshold of, for example, 0.7 may be used. In various embodiments, the correlation threshold may be chosen depending on the desired specificity and sensitivity of prediction of the physiological event. In many embodiments, cross-validation may be performed to reduce generalization errors.

Once the features are extracted and reduced, particular features may be chosen for their ability to predict pressure ulcer(s). This is followed by classification/risk estimation, at block 240, of the features to correlate them with pressure ulcer. Various classification models may then be used for classifying a future point in time as normal (no pressure ulcer) or abnormal (pressure ulcer) based on such features. For example, in an embodiment, non-probabilistic binary linear classifier support vector machine may be used. A skilled artisan will appreciate that other classification methods may be also used, alone or in combination. For example, linear classifier models such as Fisher's linear discriminant, logistic regression, naive Bayes classifier, Perceptron, may be used for classification/risk estimation. Other examples of classification models include, but are not limited to, quadratic classifiers, k-nearest neighbor kernel estimation, random forests decision trees, neural networks, Bayesian networks, Hidden Markov models, Gaussian mixture models, and so forth. In some embodiments, multi-class classification/risk estimation may also be used, if needed.

In an embodiment, at block 240, forward selection may be used to select a subset of features for optimal classification. This selection may be performed by including a cross-validation with, for example, 10 groups and allocating a particular number of events for training the model. Forward selection may start with no features followed by assessing each feature to find the best feature that correlates with the particular physiological event. Such feature may, then, be included in an optimal feature subset for appropriate classification. Selection of new features may be repeated until addition of new features does not result in improved predictive performance of the model.

Figure 14:
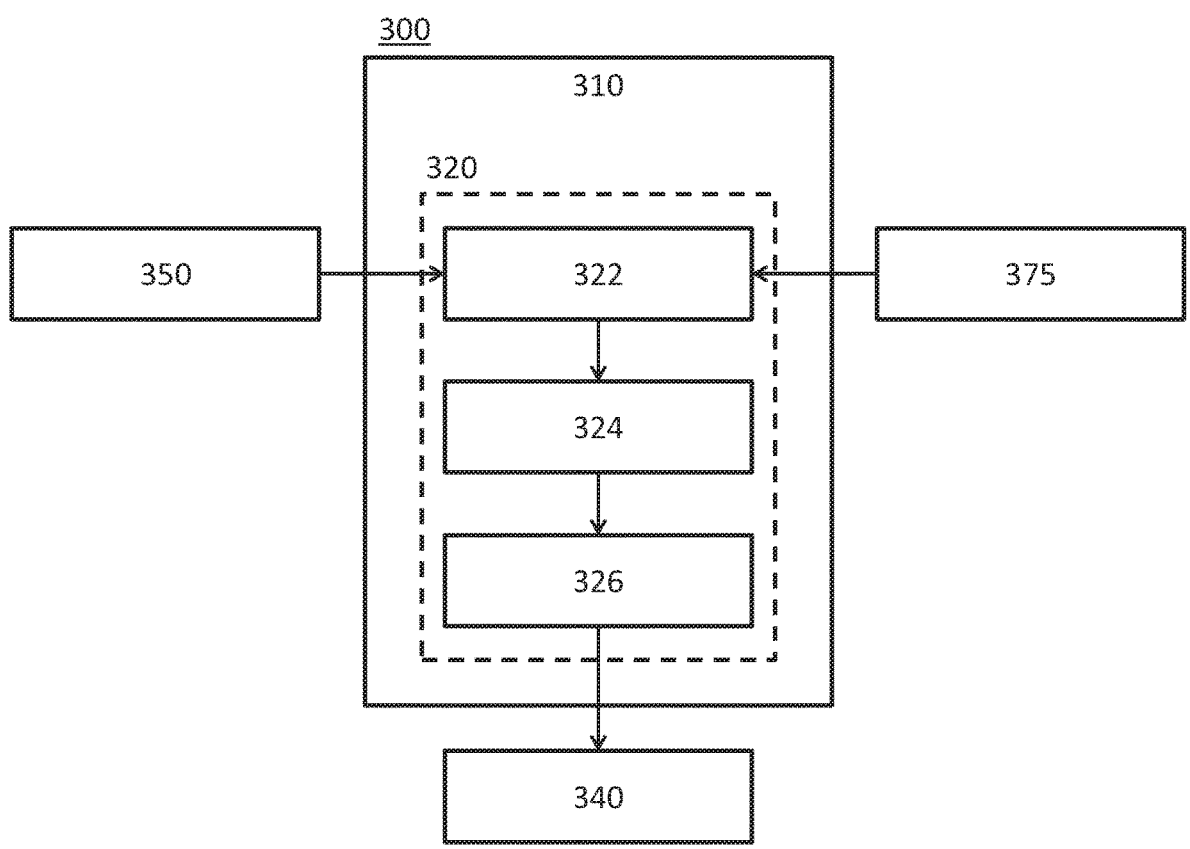
FIG. 14 depicts a block diagram of a device used for analysis of sensor data in accordance with various aspects and principles of the present disclosure.

FIG. 14 depicts a block diagram of a device used for analysis of sensor data in accordance with various aspects and principles of the present disclosure. Device 300 used for analysis of sensor data may include processor 310 configured to run algorithm 320 that enables prediction or detection of a pressure ulcer. Sensor data 350 along with at least one prior information 375 and their time of measurement are received and analyzed by algorithm 320. In some embodiments, measurements of sensor data 350 and prior information 375 may be entered manually. In other embodiments, the measurements may be transmitted automatically to processor 310 using a wired or a wireless connection to device 300. Algorithm 320 may include, calculating one or more statistical measures/mathematical derived measures, at block 322, of sensor data 350 and prior information 375 data. At block 324, the risk of pressure ulcer is estimated and analyzed for a possibility that one or more pressure ulcer(s) may develop. At block 326, an output is generated based on the analysis of block 324. For example, if it is determined, at block 324, that the risk is predominant, an alarm signal is generated at block 326. Device 300 may produce a reaction 340 based on the output generated at block 326. In various embodiments, reaction 340 may be a visual, audio, or audiovisual signal such as, for example, an alarm, a text message, a flashing light, and so forth.

In many embodiments, processor 310 may be part of a computer, a tablet, a smartphone, server application, web application, or a standalone device. In some embodiments, the device may have in-built sensors for measuring sensor data 350. In many embodiments, the device used for analyzing the sensor data may include, for example, a controlling unit (e.g., a digital signal processor or DSP), a memory (e.g., random access memory, and/or non-volatile memory), one or more sensors (e.g., IR sensors, electrodes, etc.), one or more feedback mechanisms (e.g., display, a printer, speakers, LEDs or other light sources, etc.), and/or one or more input ports.

In an embodiment, sensor data 350 may be combined, at block 322, with observational information about a subject 375 for monitoring and prediction of pressure ulcer. In such embodiments, with observational information 375 may be combined with, e.g., pressure, movement and temperature measurements 350 taken over a period prior to a discovered pressure ulcer. Patterns from the combination of sensor data and observational information may be used risk estimate the occurrence of pressure ulcer.

Figure 15A:
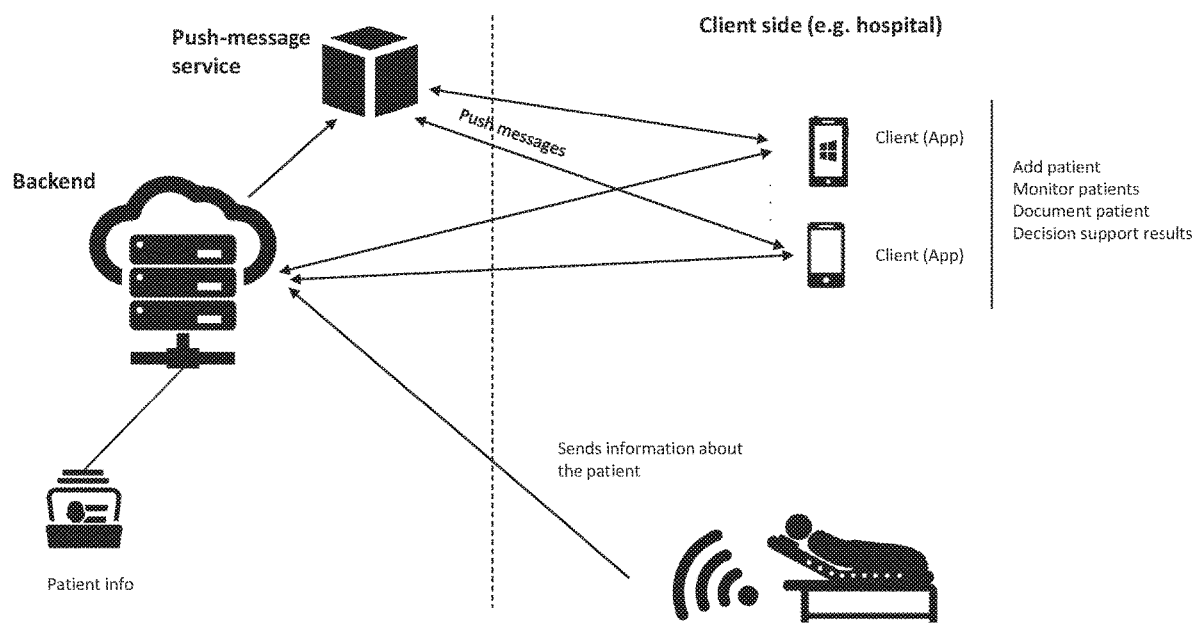
FIGS. 15a and 15b show embodiments of the system.

In an embodiment, FIG. 15a, the system is used in a hospital to estimate the risk of a particular patient's risk of developing a pressure ulcer. Pressure, movement and temperature sensors are embedded in a mattress placed underneath the patient. Sensor data from the mattress are sent every minute by a wireless connection to a server (backend). The server obtains prior information about the patient such as the patient eating pattern, mobility level, physical activity level, mental activity level, state of consciousness, oedema, age, gender, BMI or comorbidities. The sensor data and prior information are then analyzed as previously described hereby outputting risk estimation for the patient to develop a pressure ulcer within the next day or two. The risk estimation and other relevant information are directly sent to relevant caretakers at the hospital. In this embodiment the risk information is send to the caretaker's mobile phone. At the bases of the risk estimation, the caretakers can take measure to prevent the development of a pressure ulcer.

Figure 15B:
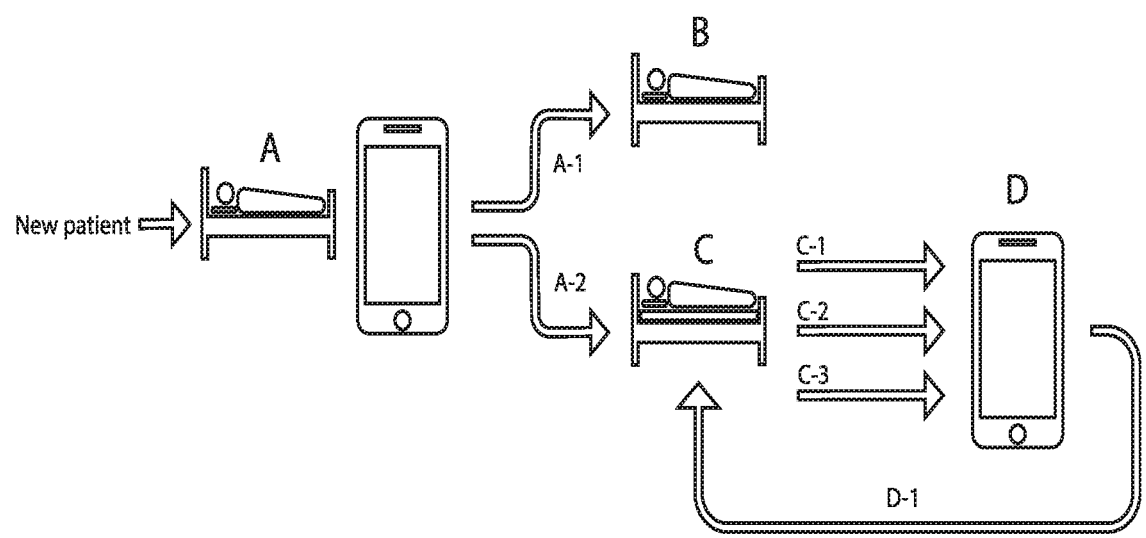

In an embodiment, FIG. 15b, show how the combination of sensors and pattern recognition algorithm a used to construct a person specific risk profile A) New Patient enters the hospital or nursing home and risk assessment is done by the PU screening algorithm tool called Q-scale. Depending on the risk assessment outcome the patient either continues as is by A-1) in B) with no PU risk or very low PU risk in the same bed without any further PU attention nor PU prevention aid. Or with either moderate or high PU risk by A-2) to C) A bed with a multi sensor mattress which is supporting different repositioning schemes and prevention aim C-1, C-2 and C-3 as well as communicating data with D) a smartphone app or other user interface. If patient movement are registered by the sensors mattress the Q-scale will automatically perform a new re-assessment of the PU risk using the Q-scale and C-1) upload new recommended PU prevention scheme and treatment with different repositioning timeframes in either the app for healthcare personal which might or might not be integrated in the EPJ, (Electronic Patient Journal) or C-2) if possible prompt the patient for repositioning with audio and light notifications through e.g. LED and buzzer sounds on or in the Q-bed mattress. Or C-3), patient reposition is performed automatically with robot or mechanical aided. E.g. supplementing to this invention with the automated third party self-turning beds, which are already on the market, or programmed robots revealing the health care personnel's need for attention and/or labor heavy workload. Especially patients with high PU risk and oversize patients are extremely labored extensive in repositioning with demands for heavy and fragile lifting. The pattern recognition algorithm in combination with the sensor mattress will over a period of time construct a user specific profile and automatically re-address the PU risk assessment e.g. detect changes to the user profile and by D-1) at least every 24 h and the results of the Q-scale may change the risk assessment into new time intervals or new PU prevention schemes and treatment.

Figure 16:
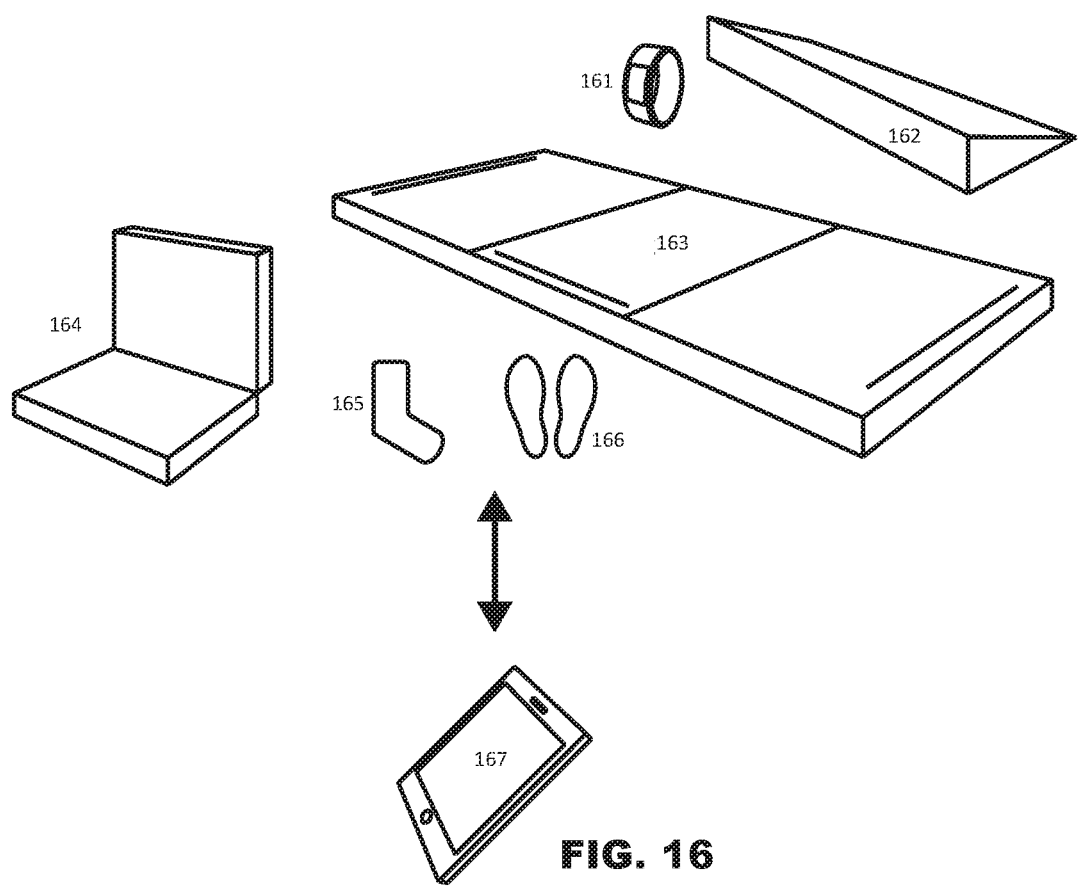
FIG. 16 depicts the person specific monitoring and feedback of the build in sensors in various embodiments.

FIG. 16 depicts various embodiments like a wristband 162, a pillow 162, a mattress 163, a seat-rest 164, a sock 165 and shoe soles 166 communicating wirelessly with a receiver/smartphone/tablet 167. The screening and monitoring algorithm is providing a prediction person specific risk with feedback to patient and healthcare personal.

In an embodiment, a method of monitoring pressure on a portion of a user's body may include measuring pressure exerted by a portion of a subject's body on one or more material filled sacs associated with a substrate having a contact surface for contacting with the portion of the subject's body to provide a pressure information, and transmitting the pressure information to a receiving station. The pressure information is used to indicate a pressure in excess of a predetermined threshold using one or more of audio, visual, audiovisual or haptic signal.

The predetermined threshold may be set by the user and/or the caregiver depending on the age, sex, weight, blood pressure, and/or other factors of the user that determine the user's risk of contracting pressure ulcers. Alternatively, a caregiver may provide such recommendation based on such or other factors deemed relevant by the caregiver.

In various embodiments, the method may be executed using the devices or systems described herein. For example, measuring pressure exerted by a user's foot may be performed using the sock described herein. Furthermore, the sock may also be used to transmit the pressure information to the controller or a receiving station of a system described herein. Likewise, in other embodiments, a user feedback device of a system described herein with reference to FIG. 8 may provide the user and/or caregiver with an indication about the excess pressure on portions of a quadriplegic patent's back.

The foregoing detailed description has set forth various embodiments of the devices and/or processes by the use of diagrams, flowcharts, and/or examples. Insofar as such diagrams, flowcharts, and/or examples contain one or more functions and/or operations, it will be understood by those within the art that each function and/or operation within such diagrams, flowcharts, or examples can be implemented, individually and/or collectively, by a wide range of hardware, software, firmware, or virtually any combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

EXAMPLES

Embodiments illustrating the devices, methods and systems described herein may be further understood by reference to the following non-limiting examples:

Example 1: Prediction of in-Hospital Pressure Ulcer Development—Clinical Validation Study Several risk scores assessing the patient's risk of developing PU have been proposed and used in medical care such as the Braden, Waterlow and Norton scale. However, the predictive values of these scales have shown low to modest accuracy. We hypothesize that PU can be prevented by dedicated early warning in high risk patients. Therefore, we investigated a new model for In-Hospital prediction of PU development.

Study design: Patients were recruited from March 2011 to September 2011. The included patients were observed from admission until discharge date. Data were collected by three research nurses, one located in each of the participating wards. The three nurses were all specialized in observing skin conditions indicative of PU development, in scientific data collection, and in preventive care. Participants: Patients aged 20 years were included in the study if they were admitted in one of three participating wards. Patients admitted and discharged within the same date were excluded from the study. Moreover, patients with PU at admission were excluded.

Data measurements: Data were obtained on the day of admission, the day after the admission, and every fourth day until discharge. Data were collected from patient medical files and by dedicated observations of each patient. Data included information on outcome, risk factors, and PU prevention activities.

Model derivation and development: A pattern classification method was developed to predict individualized development of PU into one of two classes: (1) no PU during hospitalization or (2) development of PU during hospitalization.

Logistic regression classification was chosen for foundation of the model due to the possibility of including both nominal and ordinal data types. Logistic regression utilizes a transparent decision model—this makes it attractive in a clinical setting as a decision support system. We used forward selection to include features in the model based on statistical significance. Moreover, we used 10-fold cross validation to ensure that the model was not over-fitted and that the results were transferrable to a similar cohort. We derived and tested the model on a rotating 9 (of 10) partitions of training data and 1 (of 10) partitions of test data. The accepted statistical methods ensure valid testing of the model performance and reduce generalization bias.

Validation and comparison: We evaluated the prediction models through sensitivity and specificity for pre-determined cutoff points and receiver operating characteristics (ROCS) based on logistic regression models comparing the area under the curve (AUC) of the new model.

We used another cohort for validation (N=131); this data was obtained in the same manner as the training cohort and also from the Aarhus University Hospital. In the validation cohort data scoring on the Braden scale were also obtained in these patients. We also compared our results with that of using the Braden scale for predicting the development of PU during hospitalization.

Results: A total of 383 patients were included in this study. The training data included 252 patients and the validation data included 131 patients. In the training data the mean age was 63 (.+−.SD 16) years, 36% were women, 30% of the patients were recruited from a medical unit, 51% from a Surgical unit, 19% from an Intensive Care unit. Furthermore, we observed a pressure injury incidence of 12.7%. In the validation data the mean age was 65 (.+−. SD 16) years, 34% were women, 35% of the patients were recruited from a medical unit, 47% from a Surgical unit, and 18% from an Intensive Care unit. The observed incidence for pressure injuries was 26.7%.

The training data yielded an area under the curve (AUC) of 0.82, the AUC of the validation data was also 0.82. The Qscale had a significantly higher AUC compared to that of the Braden scale with an AUC of 0.76 (p<0.05). When comparing the performance at specific thresholds for the low threshold, a specificity of 94% and a sensitivity of 47% was found (table2). This was significantly (p<0.05) better than the Braden score with a specificity of 94% and a sensitivity of 20%.

We tested a new scale for predicting PU using only simple observational data and gender of the patient. The new scale which combines observational and on-site available information regarding patient mobility, willingness and motivation could lead to an improved accuracy in predicting PU compared with a well-established method. The Braden scale is the most widely used risk scale in Denmark and therefore used for comparison in this study. For a threshold with a high specificity of 94% the new scale could improve the sensitivity significantly from 20% to 43% (Braden-scale vs Qscale). This means that the Qscale can potentially predict 43% of developing PU with few false positive. In clinical use a higher sensitivity could be chosen on the cost of specificity. This calculation of an optimal sensitivity and specificity would require a cost-benefit analysis which includes the cost of treating patients predicted to develop ulcers (true positives and false positives), the potential benefit such as reduced development of ulcers and savings. Moreover, this sensitivity of 43% would yield a positive predictive value (PPV) of 72% and a negative predictive value (NPV) of 92%. In other word this would mean that the clinicians would have to treat 10 patients and 7 of these would develop PU if no preventive measures were taken. Of course, the PPV is influenced by the incidence for having PU in a specific cohort. For instance, we observed a difference in the PPV between the training and validation results. This was primarily due to the differences in incidence rate between the two samples. In the training data we observed an incidence rate of 12.7% for the development of a PU—in the validation data we observed an incidence rate of 26.7%. Several studies have shown how the prevalence/incidence is varying between departments, this could explain the difference in incidence between the training and validation data.

The implication of identifying patients prone to developing PU during a hospital stay is to enable clinicians to target these patients with a personalized prevention plan. Patients with a high risk of PU could be treated with friction-reducing mattresses and an intensified plan for helping the patient to move or be mobilized during day and night. On the other hand patients with low risk of developing pressure ulcers might not need same level of attention for preventing PU and these patients could be checked less intensively. As described, significant resources are being used on treating pressure ulcers each year 5. If just a small percentage of these iatrogenic wounds could be avoided the hospitals would save significant resources. But this would also be of great benefit for the patients, who often suffer severely as a result of these complications. One potential usage of the proposed score could be that patients with a high risk of developing PU could receive intensive prevention measures. Such measures could include more frequent observations and assistance to change body position. Another mean could be to use a pressure-relieving sensor mattress.

Our proposed model did show a high AUC of 0.82, and this was also observed in the validation sample. However, we know that the conditions for these patients are varying from hospital to hospital and from unit to unit. We did include different types of units and validated the model on new data. Another perspective to improve the performance of these models would be to include additional hospital obtained data on the patient status. This could be results from blood samples, temperature measurements or skin pressure measurement (if the patients are using a pressure sensitive mattress). These data could be merged with the observed state of the patient to enhance the overall representation of the patient's ability to move and hereby also reduce the risk of developing PU.

We used logistic regression as a model basis. Logistic regression is often used in population modeling because population growth often follows a logistic-curve. Also, the results are easy to interpret. But it is possible that non-linear methods such as Decision tree or K-nearest neighbor may improve accuracy as these classifiers have been shown to produce reliable results in other applications.

In conclusion, we have developed and investigated a new algorithm to identify patients at risk for developing pressure ulcers during hospital-admission. Our study showed promising results on both the training, the validation data and in comparison, to the Braden scale. The new Qscale could be used in the prevention of PU in a hospital setting Example 2: A Sock for Wirelessly Monitoring Pressure on a Foot FIG. 1 shows a sock for wirelessly monitoring pressure on the foot of a patient. The sock can be made from a suitable textile fabric material such as nylon, spandex, silk, wool, cotton, polyester, and the like, or a combination thereof. A cushioning case or a pouch is stitched to the underside of the sock. The case or pouch is shaped to match the shape the underside of the sock such that a user's foot is completely cushioned by the pouch when the user wears the sock. The pouch is made from substantially the same textile fabric material as the sock. Material filled sacs made of silicone and filled with air are placed inside the pouch. The material filled sacs are provided in a meandering pattern (refer to FIG. 1) such that substantially the entire underside of the user's foot resides on at least a portion of the meandering pattern at all times while the user is wearing the sock.

An RF antenna acting as a pressure sensor is placed on the underside of one of material filled sacs such that the pressure sensor resides directly under heel of the user. A removable battery is provided for powering the RF antenna. The battery may be placed away from the underside of the foot, for example, in the sock near the ankle of the user. A wired connection may be provided from the battery to the RF antenna. A software application (App) on a smartphone communicates with the RF antenna to provide the user with a measurement of pressure on the foot on which the sock is worn. The App is configured to alert the user if the pressure is higher is normal for an extended period of time.

Example 3: Monitoring Pressure on a Foot of a Patient

A patient suffering from diabetic peripheral neuropathy in her feet is provided with a sock of Example 1. When the patient wears the sock, the material filled sacs act to cushion the foot of the patient on which the sock is worn. When the patient is in a position which exerts excess pressure on a portion of the foot, the material filled sacs under that portion of the foot redistribute the pressure throughout the surface of the foot. Additionally, the RF antenna and the pressure sensor measure the change in pressure and transmit to the smartphone application provided to the patient. The smartphone application alters the patient about the excess pressure, prompting her to change the position of her foot.

Example 4: A Sheet for Wirelessly Monitoring Pressure on the Backside of a Bed-Bound Patient FIG. 8 shows a working prototype of a sheet for wirelessly monitoring pressure on the back of a bed-bound patient, e.g., a comatose patient or a quadriplegic patient. The sheet consists of 4 distinct compartments (811-814). Each of the compartments can be made from a suitable textile fabric material such as cotton, polyester, and the like, or a combination thereof. The sheet has a length and width sufficient to extend along substantially the entire back portion of a bed-bound patient, i.e., from head to feet, such that a patient lying with their back down would cover at least a portion of the sheet. The compartments may be sized such that the patient's head and neck rest on compartment 811, the patient's upper back rests on compartment 812, the patient's lower back and hind-quarters rest on compartment 813, and the patient's legs rest on compartment 814. Inside each compartment is placed a pouch containing material filled sacs filled with silicone. The material filled sacs are provided in a meandering shape. The pouch extends substantially the entire length and width of each of the compartments.

An RF antenna acting as a pressure sensor is placed substantially at the center of each of the pouches inside and under the material filled sacs. A removable battery or other similar power source is provided for powering the RF antenna. The battery may be placed away from the portion of the compartment that is contact with the body of the patient. A wired connection may be provided from the battery to the RF antenna. A software application on a bedside monitoring device communicates with the RF antenna to provide the patient and/or a caregiver with a measurement of pressure on backside of the patient. The software application is configured to alert the patient and/or the caregiver if the pressure is higher is normal for an extended period of time.

Example 5: Monitoring the Pressure on the Backside of a Bed-Bound Patient

A comatose patient is provided with a sheet of Example 3. The patient lays backside-down on the sheet such that the material filled sacs act to cushion the backside of the patient. When the patient is in a position which exerts excess pressure on any portion of the patient's body resting on one of the compartments, e.g., a portion upper back near the scapula, the material filled sacs under that portion of the body redistribute the pressure throughout compartment on which that portion rests. Additionally, the RF antenna and the pressure sensor measure the change in pressure and transmit to the smartphone application provided to the patient. If the pressure has not been relieved over a predetermined length of time, the smartphone application alters the caregiver about the static excess pressure, prompting her to change the patients' position.

Example 6: Risk Stratification of Patients

Preliminary analysis of clinical data on 134 patients show that it is possible to stratify and predict which patients are at high risk for developing pressure ulcers during hospitalization. There are already simple scoring systems to risk stratify but as shown in the following ROC curve—which illustrate a model's ability to find the true patients with wounds from the false-positive found patients—these scoring systems (Braden and the newly developed ADHOC) are not very accurate. The blue curve shows that by using an algorithm that combines information about the patient's condition, such as the ability and willingness to mobilize themselves, physiological state, etc. it is possible to risk stratify patients more intelligent. The initial analysis indicates that it could be possible to find 8 out of 10 patients with future ulcers and that the algorithm had a false positive rate of about 15%. Furthermore, it is possible with the algorithm to analyses multiple data points simultaneously both history and real-time. And Instead of classifying patients as low- or high-risk, our system predicts the time to onset of PU for each individual patient and alerts when it is time to implement a preventive measure. Also, by mapping and analyzing the distribution of the real-time pressure and temperature measurements for the mattress, we can determine the laying orientation of each patient, as well as detect s/he has moved. This is important because a patient that switches sides when lying in a bed is redistributing/alleviating the location of the pressures and the algorithm reflects that change by readjusting the risk scores of each body part.

What is claimed is:

1. A system comprising a resting device for resting a patient, the resting device comprising:
    a substrate having a contact surface for contacting the patient, one or more sacs comprising a material and associated with the contact surface of the substrate, one or more sensors that are incorporated in the one or more sacs, and a patient recognition algorithm to detect changes in a user profile;
    wherein the system is configured to at least (a) combine information and construct the user profile, wherein the information comprises a first data from a pressure ulcer risk scale and a second data obtained via the resting device over time, and (b) automatically perform an assessment of a risk of pressure ulcer in the patient.

2. The system of claim 1, wherein the patient recognition algorithm is configured to at least predict the risk of pressure ulcer in the patient.

3. The system of claim 1, wherein the system is further configured to predict the risk of pressure ulcer in the patient using at least (a) sensor data obtained from the one or more sensors and (b) one or more prior data of the patient.

4. The system of claim 3, further comprising one or more processors that analyze the one or more prior data of the patient based on a pre-determined algorithm and produce processed data.

5. The system of claim 4, wherein the one or more processors are configured to at least (a) combine the processed data with the sensor data from the one or more sensors and (b) determine a change in the risk of pressure ulcer in the patient.

6. The system of claim 4, wherein the one or more processors are configured to preprocess the sensor data obtained from the one or more sensors to generate preprocessed data and extract one or more features from the preprocessed data, wherein the one or more features comprise distinguishing and/or informative features for classification or assessment of the risk of pressure ulcer in the patient.

7. The system of claim 6, wherein the one or more features comprise a mathematical derivative from the sensor data.

8. The system of claim 6, wherein a plurality of the one or more features are configured to form patterns that are indicative of a pressure ulcer event.

9. The system of claim 6, wherein the system is configured to extract and reduce the one or more features, and the system is further configured to choose particular features for predicting one or more pressure ulcers.

10. The system of claim 6, wherein the system is configured to extract and reduce the one or more features, and the system is further configured to classify and correlate the one or more features with one or more pressure ulcers.

11. The system of claim 10, wherein the system is configured to classify the one or more features using one or more classification models that are configured for classifying a future point in time as normal, thereby resulting in none of the one or more pressure ulcers, or abnormal, thereby resulting in the one or more pressure ulcers, based on the one or more features.

12. A system comprising a resting device for resting a patient, the resting device comprising:
   a substrate having a contact surface for contacting the patient, one or more sacs comprising a material and associated with the contact surface of the substrate, one or more sensors that are incorporated the one or more sacs, and a patient recognition algorithm to detect changes in a user profile;
   wherein the system is configured to at least (a) combine information and construct the user profile, wherein the information comprises a first data from a pressure ulcer risk scale and a second data obtained via the resting device over time, and (b) automatically perform an assessment of a risk of pressure ulcer in the patient; and
   wherein the patient recognition algorithm is configured to predict the risk of pressure ulcer in the patient using at least (a) sensor data obtained from the one or more sensors and (b) one or more observational information of the patient.

13. The system of claim 12, wherein the sensor data is combined with the one or more observational information to generate one or more patterns for estimating the risk of pressure ulcer in the patient.

14. The system of claim 12, wherein the one or more sensors comprise a pressure sensor, a movement sensor and a temperature sensor, further the system is configured to analyze the sensor data and the one or more observational information to generate the risk of pressure ulcer in the patient.

15. The system of claim 14, wherein the one or more observational information comprises one or more data of the patient, the one or more data comprising: a mobility level, a physical activity level, a mental activity level, a state of consciousness, oedema, age, gender, a body-mass index or comorbidities.

16. A system comprising a resting device for resting a patient, the resting device comprising:
   a substrate having a contact surface for contacting the patient, one or more sacs comprising a material and associated with the contact surface of the substrate, one or more sensors that are incorporated in the one or more sacs, and a patient recognition algorithm to detect changes in a user profile;
   wherein the system is configured to at least (a) combine information and construct the user profile, wherein the information comprises a first data from a pressure ulcer risk scale and a second data obtained via the resting device over time, and (b) automatically perform an assessment of a risk of pressure ulcer in the patient; and
   wherein the patient recognition algorithm is configured to predict the risk of pressure ulcer in the patient using at least (a) sensor data obtained from the one or more sensors and (b) a pattern recognition algorithm.

17. The system of claim 16, wherein the system is further configured to at least (a) detect changes in the user profile of the patient, (b) predict a potential adverse health effect on the patient and (c) undertake deployment of a pressure ulcer prevention strategy.

18. The system of claim 17, wherein the system is configured to assign the patient to the pressure ulcer prevention strategy that is commensurate with a level of the risk of pressure ulcer in the patient.

19. The system of claim 18, wherein the pressure ulcer risk scale is based on one or more observational information of the patient and gender of the patient.

20. The system of claim 19, wherein the one or more sensors comprise a pressure sensor, a movement sensor and a temperature sensor, further the system is configured to analyze the sensor data and the one or more observational information to generate the risk of pressure ulcer in the patient.

21. The system of claim 20, wherein the one or more observational information comprises one or more data of the patient, the one or more data comprising: a mobility level, a physical activity level, a mental activity level, a state of consciousness, oedema, age, gender, body-mass index or comorbidities.

* * * * *